US012600747B2

(12) United States Patent (10) Patent No.: US 12,600,747 B2
Narayan et al. (45) Date of Patent: Apr. 14, 2026

(54) PROCESS OF PURIFICATION OF PROTEIN

(71) Applicant: Kashiv BioSciences, LLC, Piscataway, NJ (US)

(72) Inventors: Om Narayan, Ahmedabad (IN); Tarun Kumar Gupta, Ahmedabad (IN); Mayankkumar Thakkar, Ahmedabad (IN)

(73) Assignee: Kashiv BioSciences, LLC, Piscataway, NJ (US)

( * ) Notice: Subject to any disclaimer, the term of this patent is extended or adjusted under 35 U.S.C. 154(b) by 0 days.

(21) Appl. No.: 19/092,641

(22) Filed: Mar. 27, 2025

(65) Prior Publication Data

US 2025/0282814 A1 Sep. 11, 2025

Related U.S. Application Data

(63) Continuation of application No. 17/922,729, filed as application No. PCT/IB2021/053658 on May 1, 2021.

(30) Foreign Application Priority Data

| May 1, 2020 | (IN) | ............................. | 202021018714 |
| May 1, 2020 | (IN) | ............................. | 202021018731 |
| May 1, 2020 | (IN) | ............................. | 202021018735 |

(51) Int. Cl.
| *C07K 1/16* | (2006.01) |
| *C07K 16/06* | (2006.01) |
| *C07K 16/42* | (2006.01) |

(52) U.S. Cl.
CPC .............. *C07K 1/16* (2013.01); *C07K 16/065* (2013.01); *C07K 16/4291* (2013.01)

(58) Field of Classification Search
None
See application file for complete search history.

(56) References Cited

U.S. PATENT DOCUMENTS

| 5,328,834 | A | 7/1994 | Ngo et al. |
| 8,703,126 | B2 | 4/2014 | Liu et al. |
| 9,291,630 | B1 | 3/2016 | Wezeman et al. |
| 9,352,035 | B2 | 5/2016 | Zhou et al. |
| 9,382,317 | B2 | 7/2016 | Manning et al. |
| 9,556,258 | B2 | 1/2017 | Nti-Gyabaah et al. |
| 9,598,718 | B2 | 3/2017 | Rupprechter et al. |
| 9,683,012 | B2 | 6/2017 | Yoon et al. |
| 10,034,940 | B2 | 7/2018 | Liu et al. |
| 10,080,793 | B2 | 9/2018 | Oever et al. |
| 10,618,960 | B2 | 4/2020 | Liu et al. |
| 12,139,510 | B2 | 11/2024 | Narayan et al. |
| 2006/0228780 | A1 | 10/2006 | Luo et al. |
| 2008/0064861 | A1 | 3/2008 | Sun |
| 2008/0167450 | A1 | 7/2008 | Pan |
| 2009/0252749 | A1 | 10/2009 | Leister et al. |
| 2010/0129379 | A1 | 5/2010 | Carpenter et al. |

| 2010/0278929 | A1 | 11/2010 | Wei et al. |
| 2011/0129468 | A1 | 6/2011 | Mccue et al. |
| 2012/0172299 | A1 | 7/2012 | Schmalz et al. |
| 2012/0322733 | A1 | 12/2012 | Shaw |
| 2013/0079498 | A1 | 3/2013 | Gilljam et al. |
| 2013/0197198 | A1 | 8/2013 | Sun et al. |
| 2013/0338344 | A1 | 12/2013 | Ramasubramanyan et al. |
| 2014/0288272 | A1 | 9/2014 | Allison et al. |
| 2014/0341843 | A1 | 11/2014 | Barnes et al. |
| 2015/0284673 | A1 | 10/2015 | Langer et al. |
| 2016/0115193 | A1 | 4/2016 | Herigstad et al. |
| 2016/0122384 | A1 | 5/2016 | Kim et al. |
| 2016/0228371 | A1 | 8/2016 | Schultz et al. |
| 2017/0007712 | A1 | 1/2017 | DeFrees et al. |
| 2017/0058019 | A1 | 3/2017 | Felföldi et al. |
| 2017/0305999 | A1 | 10/2017 | Leber et al. |
| 2017/0326069 | A1 | 11/2017 | Brunner-Schwarz et al. |
| 2018/0037642 | A1 | 2/2018 | Arakawa et al. |
| 2018/0208639 | A1 | 7/2018 | Minter et al. |
| 2018/0327446 | A1 | 11/2018 | Fong et al. |
| 2018/0333493 | A1 | 11/2018 | Shenoy |
| 2018/0344630 | A1 | 12/2018 | Igawa et al. |
| 2019/0062419 | A1 | 2/2019 | Ramasubramanyan et al. |
| 2019/0256556 | A1 | 8/2019 | Giese et al. |
| 2019/0298801 | A1 | 10/2019 | Kerwin et al. |
| 2019/0343918 | A1 | 11/2019 | Graham et al. |

(Continued)

FOREIGN PATENT DOCUMENTS

| CA | 2528906 | C | 7/2013 |
| CA | 3072129 | A1 | 3/2019 |
| CN | 103405756 | A | 11/2013 |
| CN | 103667225 | A | 3/2014 |
| CN | 106190935 | A | 12/2016 |
| CN | 109142728 | A | 1/2019 |
| WO | WO-1998/001549 | A2 | 1/1998 |
| WO | WO-2002/082066 | A1 | 10/2002 |
| WO | WO-2005/044856 | A2 | 5/2005 |
| WO | WO-2010/102241 | A1 | 9/2010 |
| WO | WO-2011/150110 | A1 | 12/2011 |

(Continued)

OTHER PUBLICATIONS

XOLAIR® (omalizumab) product insert. https://www.accessdata.fda.gov/drugsatfda_docs/label/2023/103976s5242lbl.pdf 2003.*

(Continued)

*Primary Examiner* — Nora M Rooney

(74) *Attorney, Agent, or Firm* — Goodwin Procter LLP

(57) ABSTRACT

The invention provides a process of purification of antibody or fusion protein from protein mixture comprising product and process related impurities. The process provides the use of hydroxyapatite chromatography for the separation of low molecular weight impurities and basic variants. In addition, invention further provides a scalable purification process to remove product and process related impurities.

15 Claims, 7 Drawing Sheets

(56) References Cited

U.S. PATENT DOCUMENTS

Figure 1:
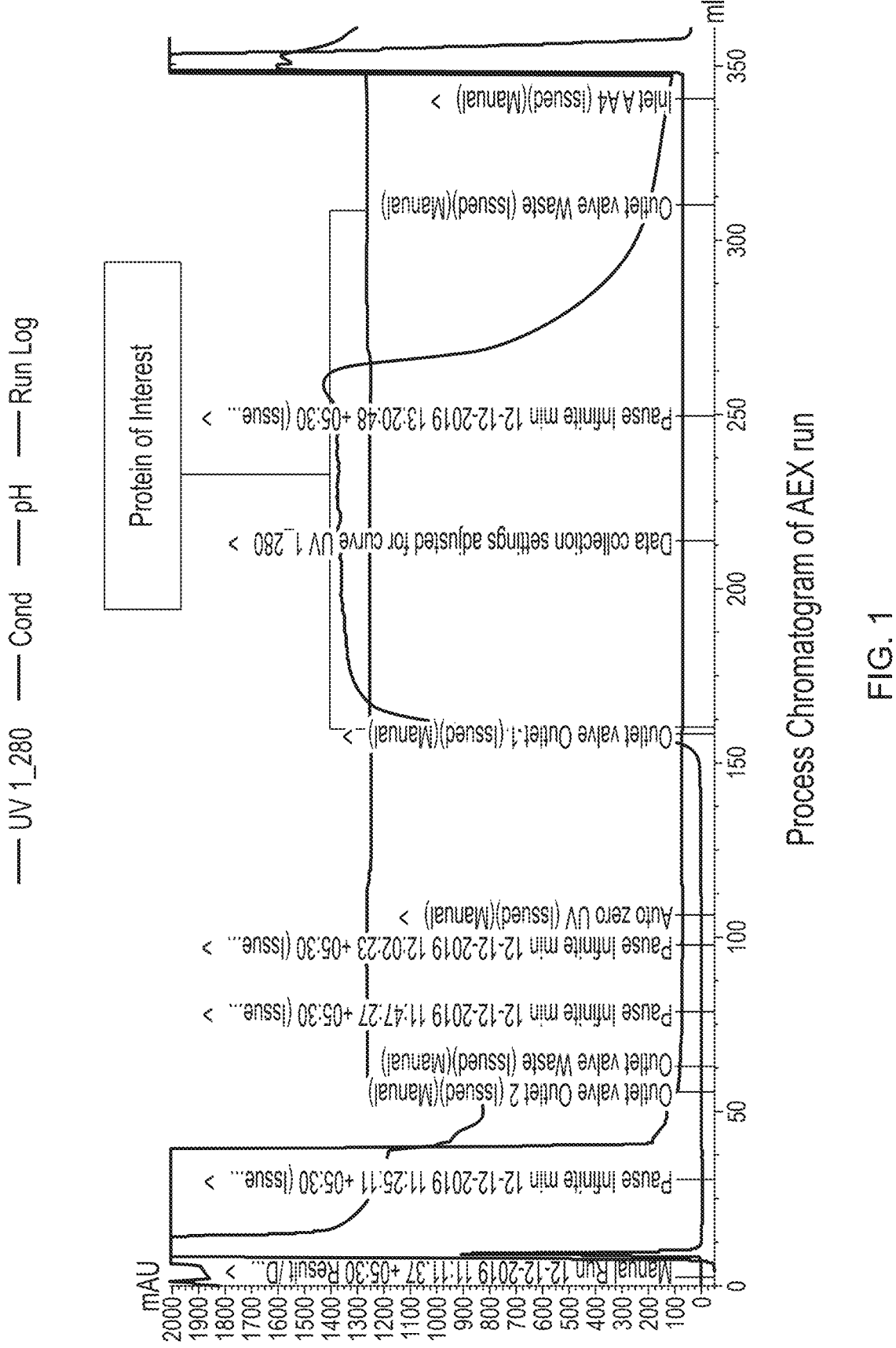

| | | |
|---|---|---|
| 2019/0353661 A1 | 11/2019 | Smith |
| 2019/0358323 A1 | 11/2019 | Liu et al. |
| 2020/0017569 A9 | 1/2020 | Leister et al. |
| 2020/0088749 A1 | 3/2020 | Salbato et al. |
| 2020/0230242 A1 | 7/2020 | Desai et al. |
| 2020/0283472 A1 | 9/2020 | Karur |
| 2021/0079422 A1 | 3/2021 | Oh et al. |
| 2021/0122782 A1 | 4/2021 | Eisenhuth et al. |
| 2021/0130396 A1 | 5/2021 | Sutter et al. |
| 2021/0230250 A1 | 7/2021 | Lazar et al. |
| 2022/0194980 A1 | 6/2022 | Leiss et al. |
| 2022/0203347 A1 | 6/2022 | Wong et al. |
| 2022/0260521 A1 | 8/2022 | Upadhyay |
| 2022/0267473 A1 | 8/2022 | Weaver et al. |
| 2023/0124565 A1 | 4/2023 | Yang et al. |
| 2023/0166200 A1 | 6/2023 | Narayan et al. |
| 2023/0166201 A1 | 6/2023 | Narayan et al. |
| 2023/0167153 A1 | 6/2023 | Narayan et al. |
| 2023/0303621 A1 | 9/2023 | Mahajan |
| 2023/0340080 A1 | 10/2023 | Sharma et al. |
| 2023/0348530 A1 | 11/2023 | Narayan et al. |
| 2024/0077483 A1 | 3/2024 | Kuppili et al. |
| 2024/0156907 A1 | 5/2024 | Narayan et al. |
| 2024/0158437 A1 | 5/2024 | Narayan et al. |
| 2024/0254160 A1 | 8/2024 | Upadhyay et al. |
| 2024/0287159 A1 | 8/2024 | Sharma et al. |
| 2024/0317799 A1 | 9/2024 | Narayan et al. |
| 2024/0343758 A1 | 10/2024 | Narayan et al. |
| 2024/0343776 A1 | 10/2024 | Narayan et al. |
| 2024/0400612 A1 | 12/2024 | Narayan et al. |
| 2025/0011395 A1 | 1/2025 | Narayan et al. |
| 2025/0043027 A1 | 2/2025 | Weaver et al. |
| 2025/0059230 A1 | 2/2025 | Upadhyay et al. |

FOREIGN PATENT DOCUMENTS

| | | |
|---|---|---|
| WO | WO-2012/160032 A1 | 11/2012 |
| WO | WO-2013/071396 A1 | 5/2013 |
| WO | WO-2013/096791 A1 | 6/2013 |
| WO | WO-2013/180647 A1 | 12/2013 |
| WO | WO-2016/009049 A1 | 1/2016 |
| WO | WO-2017/180594 A1 | 10/2017 |
| WO | WO-2019/043067 A1 | 3/2019 |
| WO | WO-2019/224842 A1 | 11/2019 |
| WO | WO-2019/224843 A1 | 11/2019 |
| WO | WO-2021/009669 A2 | 1/2021 |
| WO | WO-2021/038532 A1 | 3/2021 |
| WO | WO-2021/220251 A1 | 11/2021 |
| WO | WO-2021/220252 A1 | 11/2021 |
| WO | WO-2021/220253 A1 | 11/2021 |
| WO | WO-2021/240458 A2 | 12/2021 |
| WO | WO-2022/195505 A1 | 9/2022 |
| WO | WO-2022/201056 A1 | 9/2022 |
| WO | WO-2023/047368 A1 | 3/2023 |
| WO | WO-2023/053030 A1 | 4/2023 |
| WO | WO-2023/053031 A1 | 4/2023 |
| WO | WO-2023/053032 A1 | 4/2023 |
| WO | WO-2023/057994 A1 | 4/2023 |
| WO | WO-2023/057995 A1 | 4/2023 |
| WO | WO-2023/112000 A2 | 6/2023 |
| WO | WO-2023/180977 A1 | 9/2023 |

OTHER PUBLICATIONS

Wang et al. 'Characterization and pre-clinical assessment of a proposed biosimilar to its originator Omalizumab.' Eur. J. Pharm Sci 178(1):106292, 2022.*

Aasim et al., "The role of ligands on protein retention in adsorption chromatography: A surface energetics approach", p. 618-624, Journal of Separation Science, vol. 37, Issue 6. Jan. 21, 2014.

Ahmed et al. (1992) "Biosep-SEC-S high-performance size-exclusion chromatographic cols. for proteins and peptides," Journal of Chromatography 599:25-33.

Balbino et al., "The anti-IgE mAb omalizumab induces adverse reactions by engaging Fc receptors", J. Clin. Invest., 2020, 130(3):1330-1335.

Center for Drug Evaluation and Research et al., Product Quality Reviews 2024, FDA, pp. 1-161, https://www.accessdata.fda.gov /drugsatfda_docs/nda/2018/761075Orig 1 s000Chem R. pdf (Year: 2024).

Cohen et al., "Switching Reference Medicines to Biosimilars: A Systematic Literature Review of Clinical Outcomes", Drugs, Mar. 3, 2018, vol. 78, Iss. 4, pp. 463-478. (16 pages).

Friess et al., "Microarray-based identification of differentially expressed growth- and metastasis-associated genes in pancreatic cancer", Cellular and Molecular Life Sciences, vol. 60, Jun. 2003, pp. 1180-1199.

GE Healthcare Life Sciences (2013) Multi modal Chromatography Handbook. GE Healthcare Bio-Sciences AB, Bjorkgatan 30, 751 84 Uppsala, Sweden, 2013, pp. 1-113.

Geng et al., "Inhibition of autoregulated TGFbeta signaling simultaneously enhances proliferation and differentiation of kidney epithelium and promotes repair following renal ischemia", Am. J. Pathol., Dec. 16, 2010, vol. 174, No. 4, pp. 1291-1308.

Goke, et al. (1988) "Identification of Rat Pancreatic Secretory Proteins after Separation by High-Performance Liquid Chromatography," Pancreas 3(2): 199-206.

Gu et al. (2019) "Assessment of CE-based baseline disturbances using simulation and targeted experimental evaluation-impact on the purity determination of therapeutic proteins," Analytical and Bioanalytical Chemistry 411:2425-2437.

Guo et al. (2019) "Exploring metabolic biomarkers and regulation pathways of acute pancreatitis using ultra-performance liquid chromatography combined with a mass spectrometry-based metabolomics strategy," RSC Adv 9:12162-12173.

Guttman et al. (2020) "Better Separation Resolution of New Biopharmaceutical Modalities through Fine Tuning of the Temperature with CE-SOS" SCIEX, pp. 1-5.

Herniman et al., "Development of ultrahigh-performance liquid chromatography/mass spectrometry and ultrahigh-performance supercritical fluid chromatography/mass spectrometry assays to determine the concentration of BitrexTM and sodium saccharin in homemade facemask fit testing solutions", Rapid Communications in Mass Spectrometry, vol. 34, Iss. 16, Jun. 3, 2020, pp. 1-6.

International Search Report and Written Opinion for PCT/IB2020/ 056593 mailed Feb. 8, 2021 (10 pages).

International Search Report and Written Opinion for PCT/IB2020/ 058080 mailed Feb. 8, 2021 (12 pages).

International Search Report and Written Opinion for PCT/IB2021/ 053658 mailed Sep. 14, 2021 (15 pages).

International Search Report and Written Opinion for PCT/IB2021/ 053659 mailed Jul. 22, 2021 (9 pages).

International Search Report and Written Opinion for PCT/IB2021/ 053660 mailed Aug. 12, 2021 (10 pages).

International Search Report and Written Opinion for PCT/IB2021/ 054693 mailed Nov. 17, 2021 (7 pages).

International Search Report and Written Opinion for PCT/IB2022/ 052377 mailed Jun. 30, 2022 (8 pages).

International Search Report and Written Opinion for PCT/IB2022/ 052651 mailed Jul. 1, 2022 (11 pages).

International Search Report and Written Opinion for PCT/IB2022/ 059058 mailed Feb. 16, 2023 (8 pages).

International Search Report and Written Opinion for PCT/IB2022/ 059238 mailed Feb. 24, 2023 (12 pages).

International Search Report and Written Opinion for PCT/IB2022/ 059239 mailed Feb. 14, 2023 (7 pages).

International Search Report and Written Opinion for PCT/IB2022/ 059240 mailed Feb. 23, 2023 (13 pages).

International Search Report and Written Opinion for PCT/IB2022/ 059648 mailed Feburary 21, 2023 (8 pages).

International Search Report and Written Opinion for PCT/IB2022/ 059649 mailed Feburary 7, 2023 (8 pages).

International Search Report and Written Opinion for PCT/IB2022/ 062426 mailed Jun. 6, 2023 (8 pages).

International Search Report and Written Opinion for PCT/IB2023/ 052862 mailed Jul. 27, 2023 (8 pages).

(56) References Cited

OTHER PUBLICATIONS

Jing et al., "Separation of monocloncal antibody charge variants using cation exchange chromatography: Resins and separation conditions optimization", Separation and Purification Technology, vol. 235, Mar. 18, 2020.

Khawli et al., "Charge variants in IgG1: Isolation, characterization, in vitro binding properties and pharmacokinetics in rats", Mabs, Nov.-Dec. 2010, 2(6):613-24. doi: 10.4161/mabs.2.6.13333. (12 pages).

Lacher et al. (2010) "Development, validation, and implementation of capillary gel electrophoresis as a replacement for SDSPAGE for purity analysis of IgG2," mAbs, J. Sep. Sci. 33:218-227.

Lee et al. (2010) "Capillary Electrophoretic Separation of Poly(ethylene glycol)-Modified Granulocyte-Colony Stimulating Factor," Arch Pharm Res 22(3)491-495.

Liu et al. (2005) "Highly efficient approach for characterizing nanometer-sized gold particles by capillary electrophoresis," Analytica Chimica Acta 528: 249-254.

Lou et al., "Liquid-liquid phase separation causes high turbidity and pressure during low pH elution process in Protein A chromatography", Journal of Chromatography, Jan. 28, 2017, vol. 1488, pp. 57-67. (11 pages).

Lui et al. "(2010) Recovery and purification process development for monoclonal antibody production," mAbs 2(5):480-499.

Martias, et al. (2021) "Optimization of Sample Preparation for Metabolomics Exploration of Urine, Feces, Blood and Saliva in Humans Using Combined NMR and UHPLC-HRMS Platforms," Molecules 26(4111) 16 pages.

Molecular Probes, Protein Molecular Weight Standards (P-6649), Jan. 13, 2001, pp. 1-2.

Padfield, et al. (1986) "Separation of Guinea-Pig Pancreatic Juice Proteins by Reversed-Phase High-Performance Liquid Chromatography," Journal of Chroma. 369:133-141.

R&D Systems, Inc., "Recombinant Human CTLA 4 Fc Chimera | Catalog No. 7268-CT". Product datasheet (online). Mar. 6, 2020. (2 pages).

Sanger-van de Griend et al. (2019) "CE-SOS method development, validation, and best practice-An overview," Electrophoresis 40:2361-2374.

Shekhawat et al., "Structural similarity, characterization of Poly Ethylene Glycol linkage and identification of product related variants in biosimilar pegfilgrastim", 1-33, PLOS ONE Web. Mar. 13, 2019. (33 pages).

Singla et al., "Aggregation Kinetics for IgG1-Based Monoclonal Antibody Therapeutics", AAPS J., May 2016, 18(3):689-702. doi: 10.1208/s12248-016-9887-0. (14 pages).

Sobczak et al., "RNA structure analysis assisted by capillary electrophoresis", Nucleic Acids Research, Nov. 15, 2002, vol. 30, No. 22, e124. (8 pages).

Somerville et al. (1999) "Discrimination of granulocyte colony-stimulating factor isoforms by high-performance capillary electrophoresis," Journal of Chromatography B, 732:81-89.

Turner et al., "Development of orthogonoal NISTmAb size heterogeneity control methods", Analytical and Bioanalytical Chemistry, Mar. 2018, vol. 410, No. 8, pp. 2095-2110. (16 pages).

Voitl et al. (2010) "Application of mixed mode resins for the purification of antibodies," Journal of Chromatography A 1217:5753-5760.

Yang et al. (2015) "High resolution separation of recombinant monoclonal antibodies by size-exclusion ultra-high performance liquid chromatography (SE-UHPLC)," Journal of Pharmaceutical and Biomedical Analysis 109:52-61.

Demeule et al. (2009) "A therapeutic antibody and its antigen form different complexes in serum than in phosphate-buffered saline: A study by analytical ultracentrifugation," Analytical Biochemistry, Academic Press, Amsterdam, NL 388(2):279-287, XP026052000, ISSN: 0003-2697, DOI: 10.1016/J.AB.2009.03.012.

Degterev et al. (2011) "Improvement of the Degradation Profiling of Eculizumab and Omalizumab Monoclonal Antibodies by Liquid Chromatography-Mass Spectrometry," Journal of Analytical Chemistry 76(14):1596-1609.

Ichiuhara et al. (2018) "Integrated flow-through purification for therapeutic monoclonal antibodies processing," MABS 10(2):325-334.

Pennington et al. (2016) "Structural basis of omalizumab therapy and omalizumab-mediated IgE exchange," Nature Communications 7:11610:1-12.

Weisbjerg et al. (2015) "Serial Coupling of Ion-Exchange and Size-Exclusion Chromatography to Determine Aggregation Levels in mAbs in The Presence of a Proteinaceous Excipient, Recombinant Human Serum Albumin," Journal of Pharmaceutical Sciences 104:548-556.

XOLAI R® (omalizumab) product insert https://www.accessdata.fda.gov/drugsatfda_docs/label/2023/103976s52421bl.pdf 2003.

XOLAIR® (omalizumab) injection for subcutaneous use [package insert]. Accessdata.fda.gov. 2021. https:// www.accessdata.fda.gov/drugsatfda_docs/label/2021/103976s5238lbl.pdf (Year: 2021).

* cited by examiner

CEX-HPLC Chromatogram of AEX run (Charge Variants)

SE-HPLC Chromatogram of AEX run (Size Variants)

SE-HPLC Chromatogram of AEX run (Size Variants)- Zoomed in view

PROCESS OF PURIFICATION OF PROTEIN

CROSS-REFERENCE TO RELATED APPLICATIONS

This application is a Continuation of U.S. patent application Ser. No. 17/922,729, filed on Nov. 1, 2022, which is a U.S. National Phase Application under 35 U.S.C. § 371 of International Patent Application No. PCT/IB2021/053658, filed May 1, 2021, which claims the benefit of Indian Patent Application number 202021018714, filed on May 1, 2020, Indian Patent Application number 202021018731, filed on May 1, 2020, and Indian Patent Application number 202021018735, filed on May 1, 2020, the contents of each of which are hereby incorporated by reference in their entirety.

FIELD OF THE INVENTION

The present invention relates to hydroxyapatite chromatography to the purification of at least one antibody or fusion protein from a protein mixture containing low molecular weight impurities and basic variants.

Furthermore, the present invention provides a scalable purification process of antibody or fusion protein by using chromatography steps. More specifically the present invention provides a purified antibody composition which is pharmaceutically acceptable and substantially free of product and process related impurities.

BACKGROUND OF THE INVENTION

Monoclonal antibodies as a class of therapeutic molecules are finding an increasing demand in the biotechnology industry for the treatment of diseases. Also, these antibodies are heterogeneous in their biochemical and biophysical properties due to multiple posttranslational modification and degradation events occurs during the production. With the advancements in upstream technologies, the capacity for monoclonal antibody (mAb) production has transformed from a few milligrams to grams per liter. These titers lead to enormous pressure on downstream processes (DSPs), which need to be reworked to achieve higher efficiency and better utilization of available resources. If any of these critical parameters are not defined during the facility design stage, collapse of the process can result, further resulting in commercial loss and delaying entry of the product into the market.

A key challenge associated to successful commercialization of antibodies and fusion proteins is to develop pure product with acceptable amount of removal of product and process related impurities to comply with regulatory requirement. Product and process related impurities must be remained in the acceptable limit set by regulatory bodies for an approval. The different kind of impurities often contain unwanted components, such as size variants or charge variants. This formation of size variant, charge variant, and other undesired species, for instance, Low molecular weight aggregates (LMWs) and Basic variants respectively, which can adversely affect product safety by causing complement activation or anaphylaxis upon administration. Further, aggregate and charge variants formation may hinder manufacturing processes by causing decreased product yield, peak broadening, and loss of activity.

Hydroxyapatite chromatography is shown to be a method for chromatographically purifying monoclonal antibodies (Mab). Ceramic hydroxyapatite (CHT) chromatography is reported for the separation of HMW by using sodium chloride or calcium chloride.

In the present invention, we successfully attempted to separate low molecular weight aggregates (LMWs) and Basic Variants (BVs) from an antibody preparation using ceramic hydroxyapatite chromatography.

The present invention, we also focus on other chromatographic techniques to separate other process and product related impurities, for instance, high molecular weight aggregate (HMWs) and acidic variants.

It is reported that ion exchange and hydrophobic interaction chromatography, for instance, may induce the formation of aggregates due to an increased protein concentration or the required changes in buffer concentration and/or pH during elution. Further, in several instances antibodies show differences in isoelectric points that are too small to allow for their separation by ion-exchange chromatography. Tarditi, J. Immunol. Methods 599:13-20 (1992). However, the present invention uses anion exchange which significantly reduce high molecular weight impurity and acidic variants.

Size exclusion chromatography is cumbersome and results in the significant dilution of the product, which is a hindrance in large-scale, efficiency-based manufacturing processes. Leakage of ligands from affinity chromatography columns can also occur, which results in undesirable contamination of the eluted product. Steindl, J. Immunol. Methods 235:61-69 (2000).

There is a present need for methods of producing and purifying an antibody of interest in sufficiently pure form to be suitable for pharmaceutical use. The present invention addresses this need.

The present invention provides a scalable robust purification process which significantly reduces impurities associated with antibody or fusion proteins.

SUMMARY OF THE INVENTION

In an embodiment, the present invention provides simple, scalable, CHT process to remove at least one impurity selected from LMW, and basic variant, by using phosphate elution gradient without using NaCl, $CaCl_2$), or any other additives.

In one aspect of such embodiment, the purified protein mixture is free from or comprises minimal acceptable amount of process and product related impurities like host cell proteins, host cell DNA, leached proteins, half antibodies, clipped antibodies, dimers, tetramers, acidic or basic charge variants, aggregates, low molecular weight (LMW) species, and high molecular weights (HMW) species.

In an embodiment, the purification process provides the purity of monomer selected from more than 90% or 91% or 92% or 93% or 94% or 95% or 96% or 97% or 98% or 99%.

In an embodiment, the present invention provides a process of purifying a protein of interest from protein mixture comprising protein of interest and one or more low molecular weight (LMW) variants, the process comprising:

a. Loading the protein mixture onto Ceramic Hydroxy apatite (CHT) column with suitable buffer;
   b. Washing the CHT column with suitable buffer;
   c. Eluting the purified protein of interest with suitable gradient of phosphate buffer;

wherein the purified protein of interest is substantially pure and LMW's are below 0.4%, analysed by SE-HPLC Analysis.

In another embodiment, the present invention provides a process of purifying a protein of interest from protein mixture comprising protein of interest and one or more basic variants (BV), the process comprising:

a. Loading the protein mixture onto Ceramic Hydroxy apatite (CHT) column with suitable buffer;

b. Washing the CHT column with suitable buffer;

c. Eluting the purified protein of interest with suitable gradient of phosphate buffer;

wherein the purified protein of interest is substantially pure and basic variants are below 15% analysed by CEX-HPLC Analysis.

In an embodiment, the present invention provides a process of purifying a protein of interest from protein mixture comprising protein of interest and one or more low molecular weight (LMW) variants and one or more basic variants (BV), the process comprising:

a. Loading the protein mixture onto Ceramic Hydroxy apatite (CHT) column with suitable buffer;

b. Washing the CHT column with suitable buffer;

c. Eluting the purified protein of interest with suitable gradient of phosphate buffer;

wherein the purified protein of interest is substantially pure and LMW's are below 0.4%, analysed by SE-HPLC Analysis.

wherein the purified protein of interest is substantially pure and basic variants are below 15% analysed by CEX-HPLC Analysis.

In one aspect of such embodiment, the protein mixture eluted from CHT column comprises LMW selected from about 0.3% or less LMW, 0.2% or less LMW, 0.1% or less LMW analysed by SE-HPLC Analysis.

In one aspect of such embodiment, the protein mixture eluted from CHT column comprises low BV selected from about 14% or less BV, 13% or less BV, 12% or less BV, 11% or less BV, 10% or less BV, 9% or less BV, 8% or less BV, 7% or less BV, 6% or less BV, 5% or less BV, 4% or less BV, 3% or less BV, 2% or less BV, 1% or less BV.

In an embodiment, the present invention provides a process of purifying a protein of interest from protein mixture comprising protein of interest and low molecular weight (LMW) variant 2H1L, the process comprising:

a. Loading the protein mixture onto Ceramic Hydroxy apatite (CHT) column with suitable buffer;

b. Washing the CHT column with suitable buffer;

c. Eluting the purified protein of interest with suitable gradient of phosphate buffer;

wherein the purified protein of interest is substantially pure and 2H1L is less than 3% measured by CE-SDS.

In one aspect of such embodiment, the protein mixture eluted from CHT column comprises low 2H1L selected from about 3% or less, 2.6% or less, 2.5% or less, 2.3% or less, 2% or less, 1.7% or less, 1.5% or less, 1.4% or less.

In an embodiment, the present invention provides a process of purifying a protein of interest from protein mixture comprising protein of interest and low molecular weight (LMW) variant HH, the process comprising:

a. Loading the protein mixture onto Ceramic Hydroxy apatite (CHT) column with suitable buffer;

b. Washing the CHT column with suitable buffer;

c. Eluting the purified protein of interest with suitable gradient of phosphate buffer;

wherein the purified protein of interest is substantially pure and HH is less than 0.2% measured by CE-SDS.

In one aspect of such embodiment, the protein mixture eluted from CHT column comprises low HH is selected from about 0.2% or less, 0.24% or less, 0.21% or less, 0.15% or less, 0.12% or less, 0.09% or less or 0.08% or less, 0.06% or less or 0.04% or less and 0.03% or less.

In an embodiment, the present invention provides a process of purifying a protein of interest from protein mixture comprising protein of interest and low molecular weight (LMW) variant HC, the process comprising:

a. Loading the protein mixture onto Ceramic Hydroxy apatite (CHT) column with suitable buffer;

b. Washing the CHT column with suitable buffer;

c. Eluting the purified protein of interest with suitable gradient of phosphate buffer;

wherein the purified protein of interest is substantially pure, and HC is less than 0.4 measured by CE-SDS.

In one aspect of such embodiment, the protein mixture eluted from CHT column comprises low HC is selected from about 0.4% or less, 0.16% or less, 0.15% or less, 0.12% or less and 0.18% or less.

In an embodiment, the present invention provides a process of purifying a protein of interest from protein mixture comprising protein of interest and low molecular weight (LMW) variant LC, the process comprising:

a. Loading the protein mixture onto Ceramic Hydroxy apatite (CHT) column with suitable buffer;

b. Washing the CHT column with suitable buffer;

c. Eluting the purified protein of interest with suitable gradient of phosphate buffer;

wherein the purified protein of interest is substantially pure, and LC is reduced by 0.5% measured by CE-SDS.

In one aspect of such embodiment, the protein mixture eluted from CHT column comprises low LC selected from about 0.5% or less, 0.4% or less, 0.3% or less and 0.2 or less.

In an embodiment, the present invention provides a process of purifying a protein of interest from protein mixture comprising protein of interest and low molecular weight (LMW) variants are LC, HC, HH, and 2H1L, the process comprising:

a. Loading the protein mixture onto Ceramic Hydroxy apatite (CHT) column with suitable buffer;

b. Washing the CHT column with suitable buffer;

c. Eluting the purified protein of interest with suitable gradient of phosphate buffer;

wherein the purified protein of interest is substantially pure and LC, HC, HH, 2H1L were reduced by 3% measured by CE-SDS. In one aspect of such embodiment, the protein mixture eluted from CHT column comprises LMWs selected from LC, HC, HH and 2H1L from 2.2% to 2.6% measured by CE-SDS.

In another embodiment, the process provides linear elution gradient of CHT column wherein the concentration of phosphate is increased gradually from about 32 mM to 88 mM and thereby separate or reduce LMWs having molecular weight of about 23 kDa to about 125 kDa, and about 33% reduction in basic variant.

In another embodiment, the process provides linear elution gradient of CHT column wherein the concentration of phosphate is increased gradually from about 40 mM to 96 mM and thereby separate or reduce LMWs having molecular weight of about 23 kDa to about 125 kDa, and about 33% reduction in basic variant.

In another embodiment, the invention provides a scalable purification process at 50 L, 100 L, 200 L capable to provide substantial pure monomeric form of antibody or fusion protein and low acceptable amount of impurity selected from host cell proteins, host cell DNA, leached proteins, half antibodies, dimers, tetramers, acidic or basic charge variants, aggregates, low molecular weight (LMW) species, and high molecular weights (HMW) species.

In another embodiment, the present invention provides a process of purifying a protein of interest from protein mixture comprising protein of interest and acidic species or variant thereof, the purification process comprising:

a. Purifying the protein mixture through affinity chromatography Protein A or Protein G;

b. Subjecting the protein mixture obtained from affinity chromatography to viral inactivation;

c. Loading the protein mixture obtained from step (b) onto anion exchange resin with suitable buffer at suitable pH selected from pH 7.0 to 7.5;

d. Eluting the protein mixture in flow through mode whereby acidic species or variants of said protein of interest bind to the anion exchange resin;

wherein the eluted protein mixture obtained in step (d) comprises substantially purified protein of interest and less than 15% of acidic species or variant analysed by CEX-HPLC Analysis.

In one aspect of such embodiment, the process provides the protein mixture comprising the acidic variant is less than about 14% or less AV, 13% or less AV, 12% or less AV, 11% or less AV, 10% or less AV, 9% or less AV, 8% or less AV, 7% or less AV, 6% or less AV, 5% or less AV, 4.5% or less AV, 4% or less AV, 3% or less AV, 2% or less AV, 1% or less AV.

In another embodiment, the present invention provides a process of purifying a protein of interest from protein mixture comprising protein of interest and high molecular weight (HMW) impurity, the purification process comprising:

a. Purifying the protein mixture through affinity chromatography Protein A or Protein G;

b. Subjecting the protein mixture obtained from affinity chromatography to viral inactivation;

c. Loading the protein mixture obtained from step (b) onto anion exchange resin with suitable buffer at suitable pH selected from pH 7.0 to 7.5;

d. Eluting the protein mixture in flow through mode whereby HMW impurity binds to the anion exchange resin;

wherein the eluted protein mixture obtained in step (d) comprises substantially purified protein of interest and less than 0.5% of HMW impurity analysed by SE-HPLC Analysis.

In one aspect of such embodiment, the process provides the protein mixture comprising HMW less than 0.5% or less, about 0.4% or less or 0.3% or less or 0.2% or less or 0.1% or less.

In another embodiment, the invention provides a process of purifying the protein of interest from protein mixture comprising:

a. Obtaining protein mixture from the mammalian expression system comprising the protein of interest and at least one impurity selected from acidic variant, basic variant, low molecular weight (LMW), high molecular weight (HMW);

b. Applying the protein mixture to affinity chromatography column;

c. Eluting the protein mixture from affinity chromatography column;

d. Performing the viral inactivation of the protein mixture obtained from step (c);

e. Applying the protein mixture obtained from step (d) onto anion exchange chromatography;

f. Eluting the protein mixture in flow through mode;

g. Applying the protein mixture obtained from step (f) onto Ceramic Hydroxy apatite (CHT) column;

h. Optionally washing the CHT column with a suitable wash buffer;

i. Eluting the protein of mixture from CHT column with suitable buffer In certain embodiment, the protein of interest is IgG1 antibody or fusion proteins.

wherein the eluted protein mixture is enriched with protein of interest, and substantially free of impurities HMW, LMW's, acidic & basic variants (BV).

In an embodiment, the protein of interest is IgG1 antibody which binds to IgE. In preferred embodiment, the IgG1 antibody is biosimilar of Omalizumab.

BRIEF DESCRIPTION OF THE INVENTION

FIG. 1: depicts the Process Chromatogram of AEX run.

Figure 2:
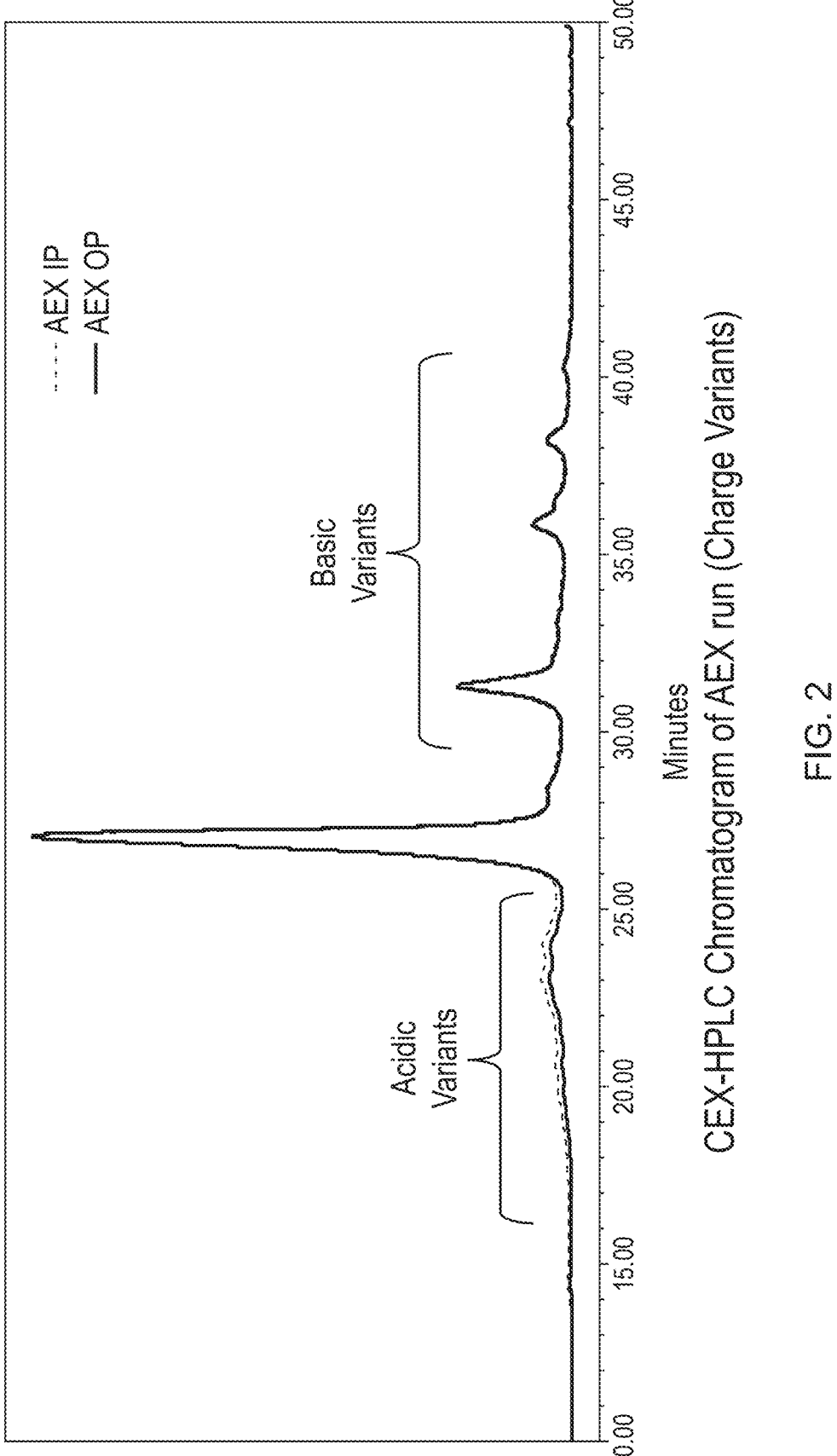

FIG. 2: depicts CEX-HPLC Chromatogram of AEX run (Charge Variants).

Figure 3:
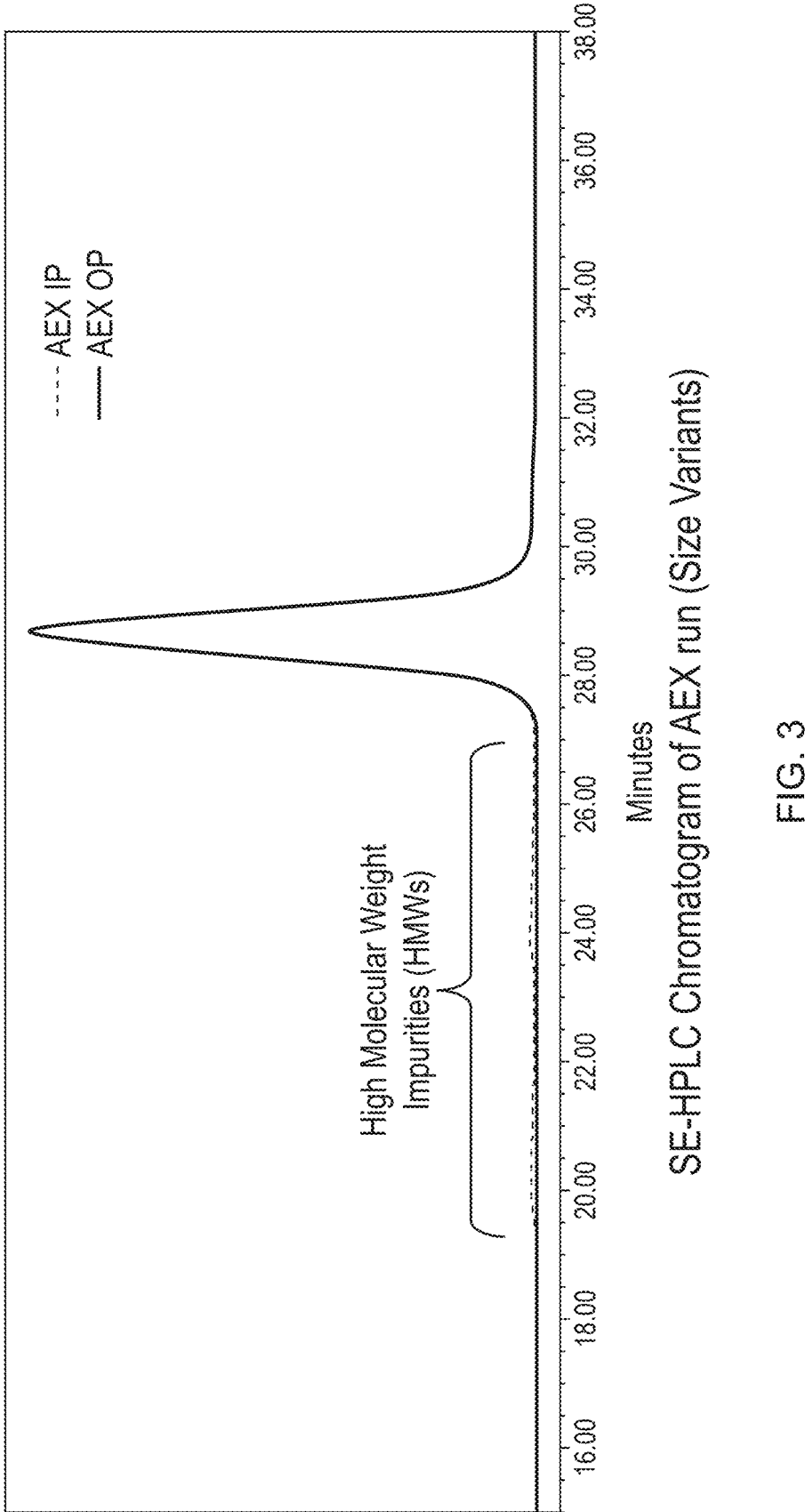

FIG. 3: depicts SE-HPLC Chromatogram of AEX run (Size Variants).

Figure 4:
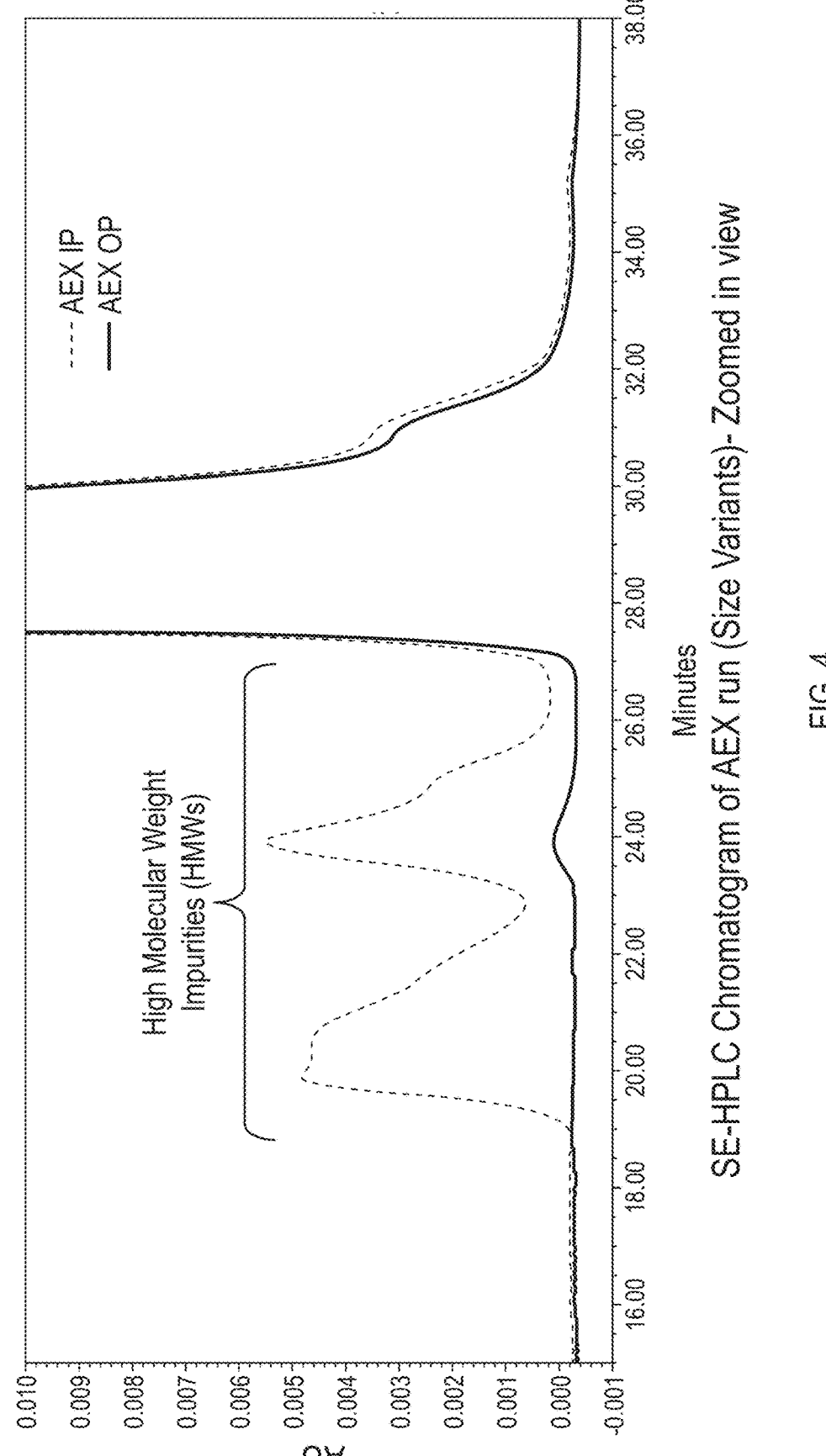

FIG. 4: depicts zoomed view of SE-HPLC Chromatogram of AEX run (Size Variants).

Figure 5:
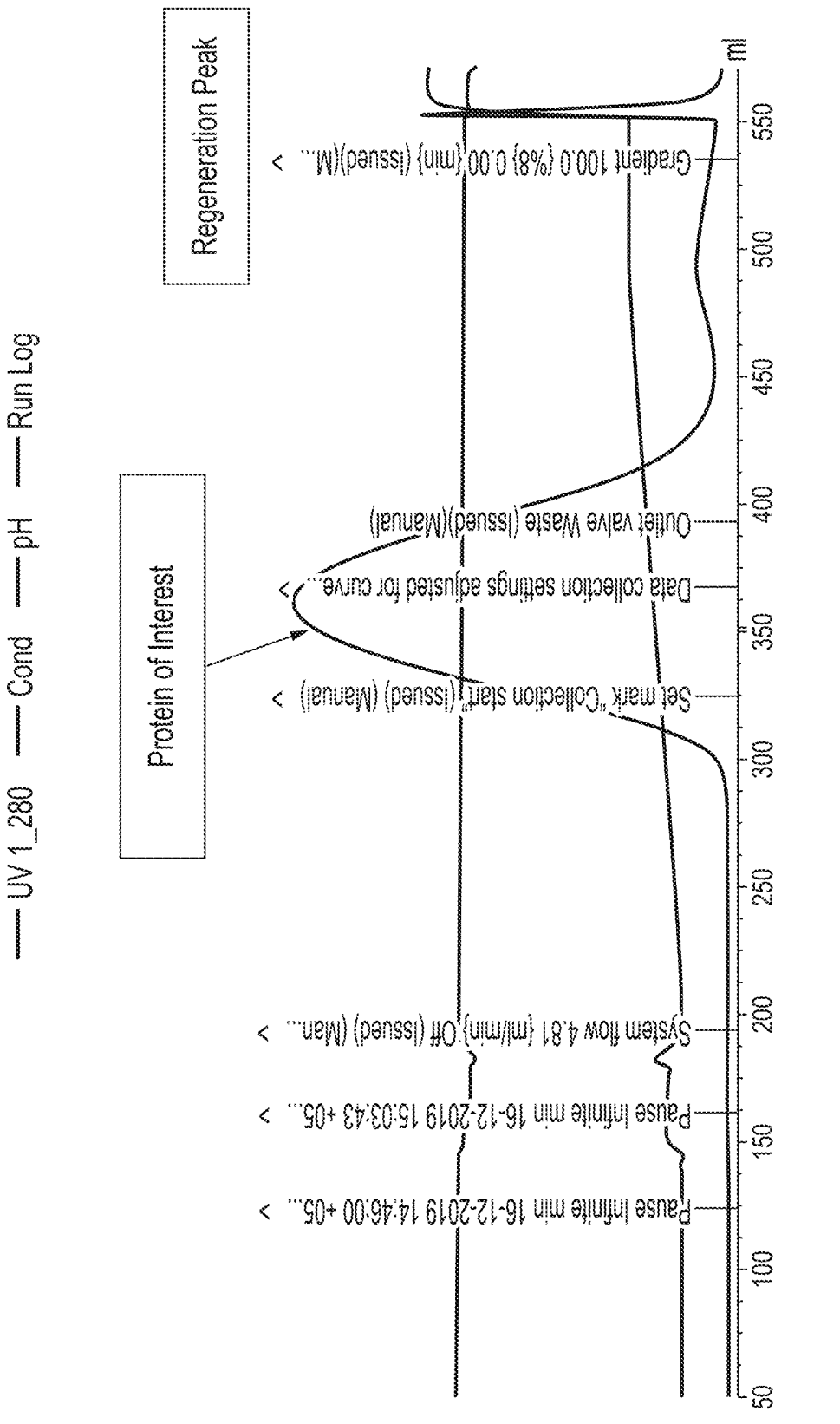

FIG. 5: depicts process chromatogram of CHT run.

Figure 6:
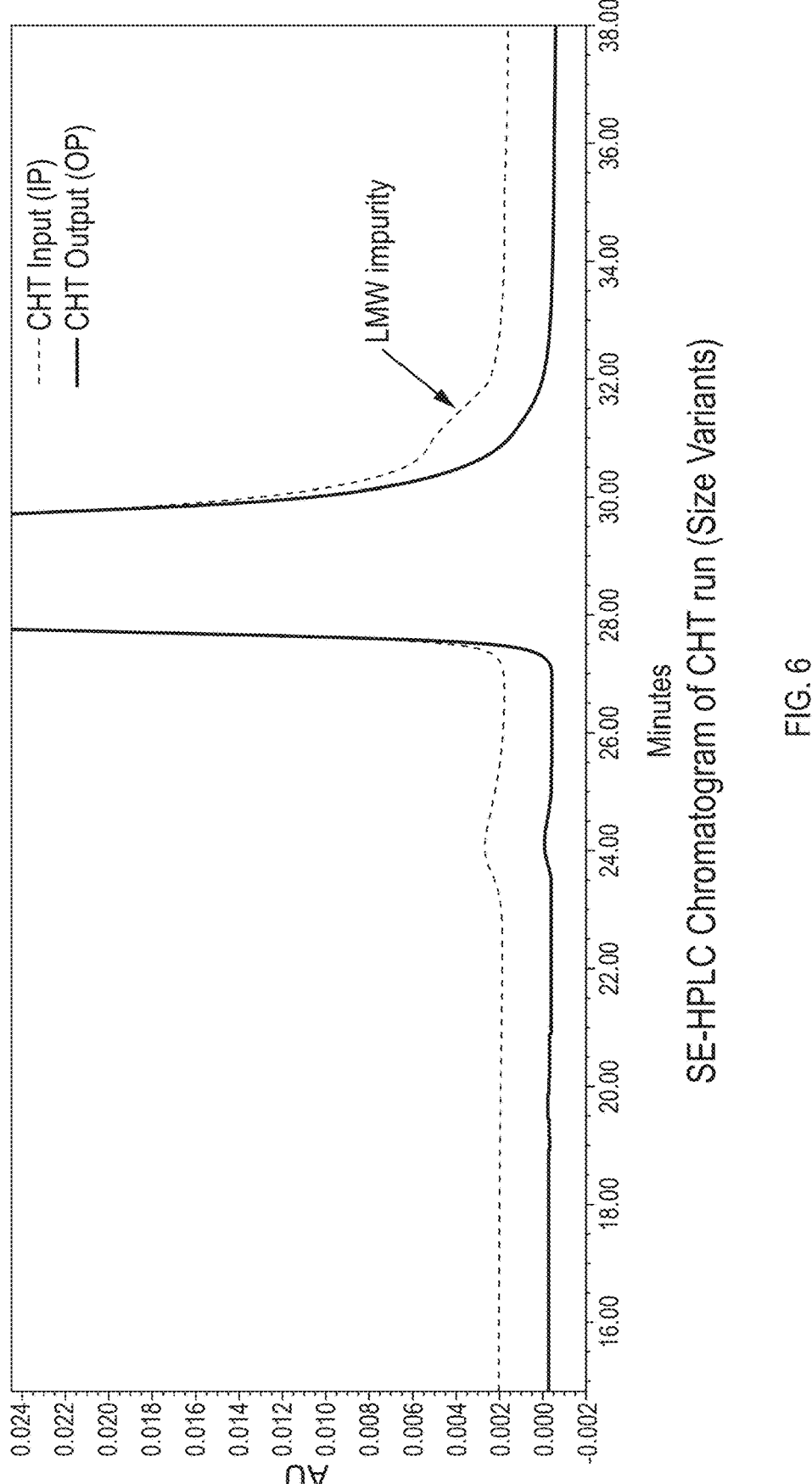

FIG. 6: depicts SE-HPLC Chromatogram of CHT run (Size Variants).

Figure 7:
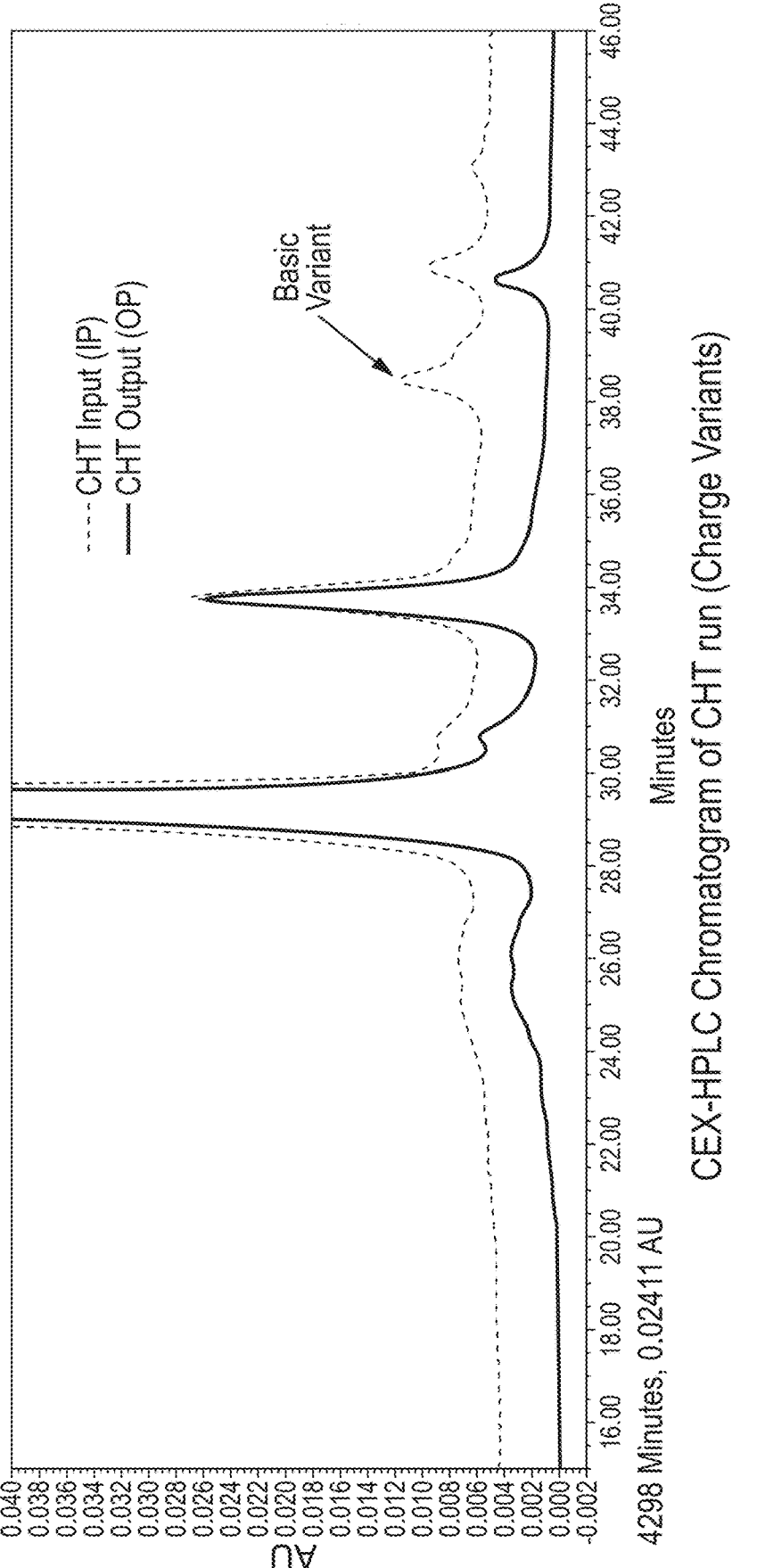

FIG. 7: CEX-HPLC Chromatogram of CHT run (Charge Variants).

DETAIL DISCUSSION OF THE INVENTION

The present invention provides a purification process which is capable to reduce various types of product and process related impurities.

In certain embodiment, the invention provides the reduction of few product related impurity by using CHT chromatography.

In certain embodiment, the invention provides the reduction of few product related impurity by using anion exchange chromatography.

In certain embodiment, the invention provides the reduction of product related impurity by using CHT and anion exchange chromatography.

In certain embodiment, the invention provides the reduction of product related impurity by using Affinity Chromatography, CHT and Anion Exchange Chromatography.

The term "antibody" includes an immunoglobulin molecule comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region (CH). The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, and FR4.

Omalizumab (Xolair®) is a recombinant DNA-derived humanized IgG1K monoclonal antibody that selectively binds to human immunoglobulin (IgE). The antibody has a molecular weight of approximately 149 kD. Xolair® is produced by a Chinese hamster ovary cell suspension culture in a nutrient medium containing the antibiotic gentamicin. Gentamicin is not detectable in the final product.

Xolair® is a sterile, white, preservative-free, lyophilized powder contained in a single-use vial that is reconstituted with Sterile Water for Injection (SWFI), USP, and administered as a subcutaneous (SC) injection.

The term "acidic variant" or "acidic species" and "AV" used herein refer to the variants of a protein, e.g., an antibody or antigen-binding portion thereof, which are characterized by an overall acidic charge. For example, in monoclonal antibody (mAb) preparations, such acidic species can be detected by various methods, such as ion exchange, for example, WCX-10 HPLC (a weak cation exchange chromatography), or IEF (isoelectric focusing). Acidic variants of antibodies are formed through Chemical and enzymatic modifications such as deamidation and sialylation, respectively, result in an increase in the net negative charge on the antibodies and cause a decrease in pI values, thereby leading to formation of acidic variants. C-terminal lysine cleavage results in the loss of net positive charge and leads to acidic variant formation. Another mechanism for generating acidic variants is the formation of various types of covalent adducts, e.g., glycation, where glucose or lactose can react with the primary amine of a lysine residue during manufacturing in glucose-rich culture media or during storage if a reducing sugar is present in the formulation. *MAbs.* 2010 November-December; 2 (6): 613 624.

The term "acidic variant" does not include process-related impurities. The term "process-related impurity," as used herein, refers to impurities that are present in a composition comprising a protein but are not derived from the protein itself. Process-related impurities include, but are not limited to, host cell proteins (HCPs), host cell nucleic acids, chromatographic materials, and media components.

The term "anion exchange chromatography" or "anion exchange column" or "AEX" used herein is a form of ion exchange chromatography (IEX), which is used to separate molecules based on their net surface charge. Anion exchange chromatography, more specifically, uses a positively charged ion exchange resin with an affinity for molecules having net negative surface charges. Anion exchange chromatography is used both for preparative and analytical purposes and can separate a large range of molecules, from amino acids and nucleotides to large proteins. Here, we focus on the preparative anion exchange chromatography of proteins.

The term "POROS 50 HQ" used herein is a Thermo Scientific™ POROS™ Strong Anion Exchange Resins (POROS AEX resins) are designed for charge-based chromatographic separation of biomolecules including recombinant proteins, monoclonal antibodies. Thermo Scientific™ POROS™ 50 HQ resin is functionalized with quaternized polyethyleneimine groups.

When "strong anion exchange" is used in flow through process the equation changes, the impurities are differentiated from the protein of interest, i.e., strong anion exchange is generally known for removal of protein A contaminant, HCP, DNA or virus in antibody purification. In a flow-through protocol, the sample and equilibration buffer are adjusted to conditions where contaminant molecules will still bind to the resin, but the protein of interest will not (because of the charge). This is achieved by increasing the salt concentration and/or increasing the pH of the buffers to a point below the pI of your molecule of interest.

As used herein the term "flow-through mode" or "flow-through" refers to purification process wherein antibody of interest does not bind to chromatographic resin. In certain embodiment the at least 50% antibody of interest does not bind to chromatographic resin. In certain embodiment the at least 60% or 70% or 80% antibody of interest does not bind to chromatographic resin. However, process and product related impurities bind the chromatographic resin. In certain embodiment the at least 50% process and product related impurities bind to chromatographic resin. In certain embodiment the at least 60% or 70% or 80% process and product related impurities bind to chromatographic resin.

As used herein the term "column" or "resin" or "chromatographic resin or chromatographic column" are interchangeable.

The term "CHT" or "ceramic hydroxyapatite chromatography" is a form of calcium phosphate used in the chromatographic separation of biomolecules. Sets of five calcium doublets (C-sites) and pairs of —OH containing phosphate triplets (P-sites) are arranged in a repeating geometric pattern. Repeating hexagonal structures can be seen in electron micrographs of the material. Space-filling models and repeat structure from Raman spectroscopy have also been constructed. Hydroxyapatite has unique separation properties and unparalleled selectivity and resolution. It often separates proteins shown to be homogeneous by electrophoretic and other chromatographic techniques.

Applications of hydroxyapatite chromatography include the purification of different subclasses of monoclonal and polyclonal antibodies, antibodies that differ in light chain composition, antibody fragments, isozymes, supercoiled DNA from linear duplexes, and single-stranded from double stranded DNA. CHT ceramic hydroxyapatite is a spherical, macroporous form of hydroxyapatite. It has been sintered at high temperatures to modify it from a crystalline to a ceramic form.

The term "substantially pure antibody" used herein includes an antibody that is substantially free of impurity selected from product or process related impurity. In certain embodiment antibody is free of acidic variant, basic variant, low molecular weight and high molecular weight, substantially pure antibody has purity less than about 99% or less than about 98% or less than about 97% or less than about 95% or less than about 92% or less than about 90% or less than about 88% or less than about 85% or less than about 82% less than about 80% or less than about 75% or less than about 70% or less than about 65% or less than about 60% or less than 50%.

The term used "Size variants" refers to LMW, HMW, or aggregates.

The term used "low molecular weight" or "LMW" species which is a protein backbone-truncated fragments & considered as product-related impurities that contribute to the size heterogeneity of antibody. LMW species often have low or substantially reduced activity relative to the monomeric form of the antibody and can lead to immunogenicity or potentially impact pharmacokinetic properties in vivo. As a result, LMW species are considered critical quality attributes that are routinely monitored during drug development and as part of release testing of purified drug product during manufacturing. The LMW has molecular weight selected from 23 kDa, 24 kDa, 25 kDa, 26 kDa, 30 kDa, 35 kDa, 40 kDa, 45 kDa, 50 kDa, 55 kDa, 60 kDa, 65 kDa, 70 kDa, 75 kDa, 80 kDa, 85 kDa, 90 kDa, 95 kDa, 100 kDa, 105 kDa, 110 kDa, 115 kDa, 120 kDa, 125 kDa, 126 kDa, and 127 kDa. In certain embodiment the LMW is selected from LC, HC, HH, and 2HL1.

The term "Light Chain" or "LC" of an antibody having a weight of 25 kDa is light or L chain. A typical antibody contains two light chain, lambda ($\lambda$) and kappa ($\kappa$). An antibody either has K chains or $\lambda$ chains, never one of each. There is no functional difference has been found between antibodies having $\lambda$ or $\kappa$ light chains, and either type of light chain can be found in antibodies of any of the five major classes. The ratio of the two types of light chain varies from species to species. However, sometime protein mixture comprises only one LC which is considered LMW impurity.

The term "Heavy Chain" or "HC" of an antibody having a weight of 50 kDa each is a heavy or H chain. There are several different types of heavy chain that define the class or isotype of an antibody. These heavy chain types vary between different animals. The heavy chains contain a series of immunoglobulin domains with one variable domain (VH) for binding an antigen and constant domains (CH1, CH2, etc.). The heavy chains with $\alpha$ and $\gamma$ have approximately 450 amino acids and the heavy chains with $\mu$ and $\varepsilon$ have approximately 550 amino acids. However, sometime protein mixture comprises only one HC which is considered LMW impurity.

The term "Two Heavy One Light Chain" or "2H1L" or "H2L" in antibody species possess a single light chain. The 2H1L species of antibody forms due to the $\beta$-elimination of a heavy chain cysteine residue, forming the inter-heavy and light chain disulfide bond, that leads to the formation of H2L species.

The term used "high molecular weight" or "HMW" is product-related impurities that contribute to the size heterogeneity of antibody products. The formation of HMW species within a therapeutic antibody drug product as a result of protein aggregation can potentially compromise both drug efficacy and safety (e.g., eliciting unwanted immunogenic response). HMW is considered critical quality attribute that are routinely monitored during drug development and as part of release testing of purified drug product during manufacturing. In certain embodiment the HMW relates to aggregates.

The term used "aggregates" are classified based on types of interactions and solubility. Soluble aggregates are invisible particles and cannot be removed with a filter. Insoluble aggregates can be removed by filtration and are often visible to the human eye. Both types of aggregates cause problems in biopharma development. Covalent aggregates arise from the formation of a covalent bond between multiple monomers of a given peptide. Disulfide bond formation of free thiols is a common mechanism for covalent aggregation. Oxidation of tyrosine residues can lead to formation of bityrosine which often results in aggregation. Reversible protein aggregation typically results from weaker protein interactions they include dimers, trimers, multimers among others.

The term used "basic variant" refers to variants can result from the presence of C-terminal lysine or glycine amidation, succinimide formation, amino acid oxidation or removal of sialic acid, which introduce additional positive charges or removal of negative charges; both types of modifications cause an increase in pI values.

The term used "high salt buffer" refers to high strength or high molality buffer.

The term used "Buffer A" and "Buffer B" is interchangeable with "first buffer" or "second buffer" respectively in CHT chromatography.

The phrase "viral reduction/inactivation", as used herein, is intended to refer to a decrease in the number of viral particles in a particular sample ("reduction"), as well as a decrease in the activity, for example, but not limited to, the infectivity or ability to replicate, of viral particles in a particular sample ("inactivation"). Such decrease in the number and/or activity of viral particles can be on the order of about 1% to about 99%, preferably of about 20% to about 99%, more preferably of about 30% to about 99%, more preferably of about 40% to about 99%, even more preferably of about 50% to about 99%, even more preferably of about 60% to about 99%, yet more preferably of about 70% to about 99%, yet more preferably of about 80% to 99%, and yet more preferably of about 90% to about 99%.

The term "comprises" or "comprising" is used in the present description, it does not exclude other elements or steps. For the purpose of the present invention, the term "consisting of" is considered to be an optional embodiment of the term "comprising of". If hereinafter a group is defined to comprise at least a certain number of embodiments, this is also to be understood to disclose a group which optionally consists only of these embodiments.

As used throughout the specification and in the appended claims, the singular forms "a," "an," and "the" include the plural reference unless the context clearly dictates otherwise.

The term "about", as used herein, is intended to refer to ranges of approximately 10-20% greater than or less than the referenced value. In certain circumstances, one of skill in the art will recognize that, due to the nature of the referenced value, the term "about" can mean more or less than a 10-20% deviation from that value.

The term "CE-SDS" is used herein to analyze LMW is selected from LC, HC, HH, and 2HL1.

The term "analytical HPLC" comprises CEX HPLC used for the estimation of charge variants and SE-HPLC for the estimation of HMWs and LMWs.

In an embodiment, the present invention provides a process of purifying a protein of interest from protein mixture comprising protein of interest and one or more low molecular weight (LMW) variants the process comprising:
    a. Loading the protein mixture onto Ceramic Hydroxy apatite (CHT) column with suitable buffer;
    b. Washing the CHT column with suitable buffer;
    c. Eluting the purified protein of interest with suitable gradient of phosphate buffer;
wherein the purified protein of interest is substantially pure and LMW's are below 0.4%, analysed by SE-HPLC Analysis.

In one aspect of such embodiment, the protein mixture eluted from CHT column comprises LMW selected from about 0.3% or less LMW, 0.2% or less LMW, 0.1% or less LMW analysed by SE-HPLC Analysis.

In an embodiment, the LMW has molecular weight selected from 23 kDa, 24 kDa, 25 kDa, 26 kDa, 30 kDa, 35 kDa, 40 kDa, 45 kDa, 50 kDa, 55 kDa, 60 kDa, 65 kDa, 70 kDa, 75 kDa, 80 kDa, 85 kDa, 90 kDa, 95 kDa, 100 kDa, 105 kDa, 110 kDa, 115 kDa, 120 kDa, 125 kDa, 126 kDa, and 127 kDa.

In another embodiment, the present invention provides a process of purifying a protein of interest from protein mixture comprising protein of interest and one or more basic variants (BV), the process comprising:
    a. Loading the protein mixture onto Ceramic Hydroxy apatite (CHT) column with suitable buffer;
    b. Washing the CHT column with suitable buffer;
    c. Eluting the purified protein of interest with suitable gradient of phosphate buffer;
wherein the purified protein of interest is substantially pure and basic variants are below 15% analysed by CEX-HPLC Analysis.

In one aspect of such embodiment, the protein mixture eluted from CHT column comprises low BV selected from about 14% or less BV, 13% or less BV, 12% or less BV, 11% or less BV, 10% or less BV, 9% or less BV, 8% or less BV, 7% or less BV, 6% or less BV, 5% or less BV, 4% or less BV, 3% or less BV, 2% or less BV, 1% or less BV.

In an embodiment, the present invention provides a process of purifying a protein of interest from protein mixture comprising protein of interest and one or more low molecular weight (LMW) variants and one or more basic variants (BV), the process comprising:

a. Loading the protein mixture onto Ceramic Hydroxy apatite (CHT) column with suitable buffer;

b. Washing the CHT column with suitable buffer;

c. Eluting the purified protein of interest with suitable gradient of phosphate buffer;

wherein the purified protein of interest is substantially pure and LMW's are below 0.4%, analysed by SE-HPLC Analysis;

wherein the purified protein of interest is substantially pure and basic variants are below 15% analysed by CEX-HPLC Analysis.

In one aspect of such embodiment, the protein mixture eluted from CHT column comprises LMW selected from about 0.3% or less LMW, 0.2% or less LMW, 0.1% or less LMW analysed by SE-HPLC Analysis.

In one aspect of such embodiment, the protein mixture eluted from CHT column comprises low BV selected from about 14% or less BV, 13% or less BV, 12% or less BV, 11% or less BV, 10% or less BV, 9% or less BV, 8% or less BV, 7% or less BV, 6% or less BV, 5% or less BV, 4% or less BV, 3% or less BV, 2% or less BV, 1% or less BV.

In an embodiment, the present invention provides a process of purifying a protein of interest from protein mixture comprising protein of interest and low molecular weight (LMW) variant 2H1L, the process comprising:

a. Loading the protein mixture onto Ceramic Hydroxy apatite (CHT) column with suitable buffer;

b. Washing the CHT column with suitable buffer;

c. Eluting the purified protein of interest with suitable gradient of phosphate buffer;

wherein the purified protein of interest is substantially pure and 2H1L is less than 3% measured by CE-SDS.

In one aspect of such embodiment, the protein mixture eluted from CHT column comprises low 2H1L selected from about 3% or less, 2.6% or less, 2.5% or less, 2.3% or less, 2% or less, 1.7% or less, 1.5% or less, 1.4% or less.

In an embodiment, the present invention provides a process of purifying a protein of interest from protein mixture comprising protein of interest and low molecular weight (LMW) variant HH, the process comprising:

a. Loading the protein mixture onto Ceramic Hydroxy apatite (CHT) column with suitable buffer;

b. Washing the CHT column with suitable buffer;

c. Eluting the purified protein of interest with suitable gradient of phosphate buffer;

wherein the purified protein of interest is substantially pure and HH is less than 0.2% measured by CE-SDS.

In one aspect of such embodiment, the protein mixture eluted from CHT column comprises low HH is selected from about 0.2% or less, 0.24% or less, 0.21% or less, 0.15% or less, 0.12% or less, 0.09% or less or 0.08% or less, 0.06% or less or 0.04% or less and 0.03% or less.

In an embodiment, the present invention provides a process of purifying a protein of interest from protein mixture comprising protein of interest and low molecular weight (LMW) variant HC, the process comprising:

a. Loading the protein mixture onto Ceramic Hydroxy apatite (CHT) column with suitable buffer;

b. Washing the CHT column with suitable buffer;

c. Eluting the purified protein of interest with suitable gradient of phosphate buffer;

wherein the purified protein of interest is substantially pure, and HC is less than 0.4 measured by CE-SDS.

In one aspect of such embodiment, the protein mixture eluted from CHT column comprises low HC is selected from about 0.4% or less, 0.16% or less, 0.15% or less, 0.12% or less and 0.18% or less.

In an embodiment, the present invention provides a process of purifying a protein of interest from protein mixture comprising protein of interest and low molecular weight (LMW) variant LC, the process comprising:

a. Loading the protein mixture onto Ceramic Hydroxy apatite (CHT) column with suitable buffer;

b. Washing the CHT column with suitable buffer;

c. Eluting the purified protein of interest with suitable gradient of phosphate buffer;

wherein the purified protein of interest is substantially pure, and LC is reduced by 0.5% measured by CE-SDS.

In one aspect of such embodiment, the protein mixture eluted from CHT column comprises low LC selected from about 0.5% or less, 0.4% or less, 0.3% or less and 0.2 or less.

In an embodiment, the present invention provides a process of purifying a protein of interest from protein mixture comprising protein of interest and low molecular weight (LMW) variants are LC, HC, HH, and 2H1L, the process comprising:

a. Loading the protein mixture onto Ceramic Hydroxy apatite (CHT) column with suitable buffer;

b. Washing the CHT column with suitable buffer;

c. Eluting the purified protein of interest with suitable gradient of phosphate buffer;

wherein the purified protein of interest is substantially pure and LC, HC, HH, and 2H1L were reduced by 3% measured by CE-SDS.

In one aspect of such embodiment, the protein mixture eluted from CHT column comprises LMWs LC, HC, HH and 2H1L from 2.2% to 2.6% measured by CE-SDS.

In another embodiment, the process provides linear elution gradient of CHT column wherein the concentration of phosphate is increased gradually from about 32 mM to 88 mM and thereby separate or reduce LMWs having molecular weight of about 23 kDa to about 125 kDa, and about 33% reduction in basic variant.

In another embodiment, the process provides linear elution gradient of CHT column wherein the concentration of phosphate is increased gradually from about 40 mM to 96 mM and thereby separate or reduce LMWs having molecular weight of about 23 kDa to about 125 kDa, and about 33% reduction in basic variant.

In an embodiment, the present invention provides a process of purifying a protein of interest from protein mixture comprising protein of interest and one or more low molecular weight (LMW) variants and one or more basic variants (BV), the process comprising:

a. Loading the protein mixture onto Ceramic Hydroxy apatite (CHT) column with suitable buffer;

b. Washing the CHT column with suitable buffer;

c. Eluting the purified protein of interest with suitable gradient of phosphate buffer;

wherein the purified protein of interest is substantially pure and LMW's are below 0.4%, analysed by SE-HPLC Analysis.

In an embodiment, the purification process reduces LMW at least by about less than about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81%, about 80%, about 75%, about 70%, about 65%, about 60%, about 55% and about 50% or less.

In an embodiment, the present invention provides a process of purifying a protein of interest from protein mixture comprising protein of interest and one or more basic variants (BV), the process comprising:

a. Loading the protein mixture onto Ceramic Hydroxy apatite (CHT) column with suitable buffer;

b. Washing the CHT column with suitable buffer;

c. Eluting the purified protein of interest with suitable gradient of phosphate buffer;

wherein the purified protein of interest protein is substantially pure, and basic variants are below 15% analysed by CEX-HPLC Analysis.

In an embodiment, the purification process reduces basic variant at least by about 5% or about 10% or about 15% or about 20% or about 25% or about 30% or about 31% or about 32% or about 33% or about 34%, about, 35%, about 40% or about 45% and about 50%.

In preferred embodiment, the purification process reduces basic variant at least by about 33%.

In another embodiment, the purification process reduces basic variant at scale of 5 L, or 50 L or 100 L or 200 L at least by about 33%.

In another embodiment, the invention provides a scalable purification process at 5 L, 50 L, 100 L, and 200 L capable to provide substantial pure monomeric form of antibody or fusion protein and low acceptable amount of impurity selected from host cell proteins, host cell DNA, leached proteins, half antibodies, dimers, tetramers, acidic or basic charge variants, aggregates, low molecular weight (LMW) species, and high molecular weights (HMW) species.

The invention provides a robust standardized purification process which is capable to utilize from small (5 L) to high scale 50 L-200 L or higher with same efficiency and provide uniform result, thereby also providing for reliable product quality. A further advantage herein is the ability to develop effective and reliable regulatory compliant (such as in terms of US FDA and/or EMA standards) protein of interest such as antibody or fusion protein.

In certain embodiment, the loading, washing and elution steps of CHT column completes within about 30 min to about 105 min. In certain embodiment, the loading, washing and elution steps of CHT column completes within 104 min.

In certain embodiments, the mammalian cell is a CHO cell.

In an embodiment, wherein the loading, washing, and elution buffer does not have any additive selected from sodium chloride, calcium chloride, and glycine.

In an embodiment, wherein the suitable buffer is a Polar Protic Molecule, Sodium Phosphate, Tris, and HEPES etc.

In an embodiment, wherein the loading, washing and elution buffer have pH ranging from about 6.5 to about 7.2.

In an embodiment, wherein the loading, washing and elution buffer have pH 7.0±0.2.

In an embodiment, the loading and washing buffer has conductivity range from about 3 to about 7 mS/cm.

In preferred embodiment, wherein the loading and washing buffer have conductivity about 6 mS/cm.

In another embodiment, wherein the elution phosphate gradient is a linear gradient wherein the concentration of phosphate is increased gradually from about 5% to 25% of buffer B.

In another embodiment, wherein the process wherein the concentration of phosphate is increased gradually from about 8% to 22%.

In another embodiment, wherein the process wherein the concentration of phosphate is increased gradually from about 10% to 24%.

In one aspect of such embodiment, wherein the protein mixture eluted from CHT column comprises LMW below 0.4%, analysed by SE-HPLC Analysis.

In one aspect of such embodiment, wherein the protein mixture eluted from CHT column comprises LMW selected from about 0.3% or less LMW, 0.2% or less LMW, 0.1% or less LMW analysed by SE-HPLC Analysis.

In one aspect of such embodiment, wherein the protein mixture eluted from CHT column comprises low BV selected from about 14% or less BV, 13% or less BV, 12% or less BV, 11% or less BV, 10% or less BV, 9% or less BV, 8% or less BV, 7% or less BV, 6% or less BV, 5% or less BV, 4% or less BV, 3% or less BV, 2% or less BV, 1% or less BV.

In one aspect of such embodiment, wherein the protein mixture eluted from CHT column comprises less than 10% BV.

In another embodiment, wherein the process provides the linear elution gradient wherein the concentration of phosphate is increased gradually from about 24 mM to 100 mM.

In another embodiment, wherein the process provides linear elution gradient of CHT column wherein the concentration of phosphate is increased gradually from about 32 mM to 88 mM.

In another embodiment, wherein the process provides linear elution gradient of CHT column wherein the concentration of phosphate is increased gradually from about 40 mM to 96 mM.

In an embodiment, the present invention provides a process of purifying an antibody binds to IgE from protein mixture comprising said antibody and one or more low molecular weight (LMW) variants and one or more basic variants (BV), the process comprising:

a. Loading the protein mixture onto Ceramic Hydroxy apatite (CHT) column with suitable buffer;

b. Washing the CHT column with suitable buffer;

c. Eluting the purified protein of interest with suitable gradient of phosphate buffer;

wherein the purified antibody is substantially pure and LMW's are below 0.4%, analysed by SE-HPLC Analysis; wherein the purified antibody is substantially pure and basic variants are below 15% analysed by CEX-HPLC Analysis.

In one aspect of such embodiment, the antibody eluted from CHT column comprises LMW selected from about 0.3% or less LMW, 0.2% or less LMW, 0.1% or less LMW analysed by SE-HPLC Analysis.

In one aspect of such embodiment, the antibody eluted from CHT column comprises low BV selected from about 14% or less BV, 13% or less BV, 12% or less BV, 11% or less BV, 10% or less BV, 9% or less BV, 8% or less BV, 7% or less BV, 6% or less BV, 5% or less BV, 4% or less BV, 3% or less BV, 2% or less BV, 1% or less BV.

In certain embodiment, the protein of interest is IgG1 antibody or fusion proteins. In an embodiment, the protein of interest is IgG1 antibody which binds to IgE. In preferred embodiment, the IgG1 antibody is biosimilar of Omalizumab.

In an embodiment, the purification process provides the purity of monomer selected from more than 90% or 91% or 92% or 93% or 94% or 95% or 96% or 97% or 98% or 99%.

In an embodiment, the invention provides a pharmaceutical purified composition of Omalizumab comprising substantially purified monomer of said Omalizumab and LMW less than about 0.2% measure by SE-HPLC.

In another embodiment, the invention provides a pharmaceutical purified composition of Omalizumab purified by CHT chromatography comprising substantially purified monomer of said Omalizumab and LMW less than about 0.2% measure by SE-HPLC.

In another embodiment, the invention provides a pharmaceutical purified composition of Omalizumab purified by CHT chromatography comprising substantially purified monomer of said Omalizumab and LMWs selected from LC, HC, HH and 2H1L from 2.2% to 2.6% measured by CE-SDS.

In another embodiment, the invention provides a pharmaceutical purified composition of Omalizumab comprising substantially purified monomer of said Omalizumab and basic variant less than 5% measure by CEX-HPLC.

In another embodiment, the invention provides a pharmaceutical purified composition of Omalizumab purified by CHT chromatography comprising substantially purified monomer of said Omalizumab and basic variant less than 5% measure by CEX-HPLC.

In another embodiment, the present invention provides a process of purifying a protein of interest from protein mixture comprising protein of interest and acidic species or variant thereof, the purification process comprising:
- a. Loading the protein mixture onto anion exchange resin with suitable buffer at suitable pH selected from pH 7.0 to 7.5;
- b. Eluting the protein mixture in flow through mode whereby acidic species or variants of said protein of interest bind to the anion exchange resin;

wherein the eluted protein mixture comprises substantially pure monomer of the protein of interest and less than 15% of acidic species or variant analysed by CEX-HPLC Analysis.

In one aspect of such embodiment, the process provides the protein mixture comprising the acidic variant is less than about 14% or less AV, 13% or less AV, 12% or less AV, 11% or less AV, 10% or less AV, 9% or less AV, 8% or less AV, 7% or less AV, 6% or less AV, 5% or less AV, 4.5% or less AV, 4% or less AV, 3% or less AV, 2% or less AV, 1% or less AV.

In another embodiment, the invention provides a pharmaceutical purified composition of Omalizumab comprising substantially purified monomer of said Omalizumab and acidic variant less than 12% measure by CEX-HPLC.

In another embodiment, the invention provides a pharmaceutical purified composition of Omalizumab purified by AEX chromatography comprising substantially purified monomer of said Omalizumab and acidic variant less than 12% measure by CEX-HPLC.

In another embodiment, the invention provides a pharmaceutical purified composition of Omalizumab purified by AEX chromatography comprising substantially purified monomer of said Omalizumab and acidic variant less than 10% measure by CEX-HPLC.

In another embodiment, the present invention provides a process of purifying an protein of interest from the protein mixture comprising protein of interest and high molecular weight (HMW) impurity, the purification process comprising:
- a. Loading the protein mixture obtained onto anion exchange resin with suitable buffer at suitable pH selected from pH 7.0 to 7.5;
- b. Eluting the protein mixture in flow through mode whereby HMW impurity binds to the anion exchange resin;

wherein the eluted protein mixture comprises substantially pure monomer of the protein of interest and less than 0.5% of HMW impurity analysed by SE-HPLC Analysis.

In one aspect of such embodiment, the process provides the protein mixture comprising HMW less than 0.5% or less, about 0.4% or less or 0.3% or less or 0.2% or less or 0.1% or less.

In another embodiment, the invention provides a pharmaceutical purified composition of Omalizumab purified by AEX chromatography comprising substantially purified monomer of said Omalizumab and HMW less than 0.5% measure by SE-HPLC.

In another embodiment, the present invention provides a process of purifying a protein of interest from protein mixture comprising protein of interest and acidic species or variant thereof, the purification process comprising:
- a. Purifying the protein mixture through affinity chromatography Protein A or Protein G;
- b. Subjecting the protein mixture obtained from affinity chromatography to viral inactivation;
- c. Loading the protein mixture obtained from step (b) onto anion exchange resin with suitable buffer at suitable pH selected from pH 7.0 to 7.5;
- d. Eluting the protein mixture in flow through mode whereby acidic species or variants of said protein of interest bind to the anion exchange resin;

wherein the eluted protein mixture obtained in step (d) comprises substantially pure monomer of the protein of interest and less than 15% of acidic species or variant analysed by CEX-HPLC Analysis.

In one aspect of such embodiment, the process provides the protein mixture comprising the acidic variant is less than about 14% or less AV, 13% or less AV, 12% or less AV, 11% or less AV, 10% or less AV, 9% or less AV, 8% or less AV, 7% or less AV, 6% or less AV, 5% or less AV, 4.5% or less AV, 4% or less AV, 3% or less AV, 2% or less AV, 1% or less AV.

In one aspect of such embodiment, the purification process reduces acidic variant at least by 40% preferably by 50% in protein mixture obtained in flow through mode of strong anion exchange.

In another embodiment, the present invention provides a process of purifying a protein of interest from protein mixture comprising protein of interest and high molecular weight (HMW) impurity, the purification process comprising:
- a. Purifying the protein mixture through affinity chromatography Protein A or Protein G;
- b. Subjecting the protein mixture obtained from affinity chromatography to viral inactivation;
- c. Loading the protein mixture obtained from step (b) onto anion exchange resin with suitable buffer at suitable pH selected from pH 7.0 to 7.5;
- d. Eluting the protein mixture in flow through mode whereby HMW impurity binds to the anion exchange resin;

wherein the eluted protein mixture obtained in step (d) comprises substantially pure monomer of the protein of interest and less than 0.5% of HMW impurity analysed by SE-HPLC Analysis.

In one aspect of such embodiment, the process provides the protein mixture comprising HMW less than 0.5% or less, about 0.4% or less or 0.3% or less or 0.2% or less or 0.1% or less.

In one aspect of such embodiment, the purification process reduces HMW at least by 80% preferably by 90% in protein mixture obtained in flow through mode of strong anion exchange.

In an embodiment, the present invention surprisingly found the removal of acidic variants and HMW through strong anion exchange column by performing the column in flow-through mode wherein the buffer solution pH is 7.0 to 7.3 marginally below than the pI of the omalizumab. The optimization of the desired pH of buffer leads to the substantial binding at least more than 40% of acidic variant or HMW to strong anion exchange. In certain embodiment the more than 80% HMW binds to strong anion exchange.

In an embodiment, the present invention provides the purified antibody composition obtained from strong anion exchange wherein the acidic variants are less than 15% preferably less than 12% and HMW less than 0.5% preferably 0.3% which is under the acceptable limitation of regulatory bodies.

In an embodiment, the present invention is very useful in reducing the burden in downstream processing by avoiding the use of multiple columns. In certain embodiment, the present invention avoids the use HIC, and multimodal chromatography.

In another embodiment, the invention provides a process of purifying the protein of interest from protein mixture comprising:
- a. Obtaining protein mixture from the mammalian expression system comprising the protein of interest and at least one impurity selected from acidic variant, basic variant, low molecular weight (LMW), high molecular weight (HMW); Applying the protein mixture to affinity chromatography column;
- b. Eluting the protein mixture from affinity chromatography column;
- c. Performing the viral inactivation of the protein mixture obtained from step (c);
- d. Applying the protein mixture obtained from step (d) onto anion exchange chromatography;
- e. Eluting the protein mixture in flow through mode;
- f. Applying the protein mixture substantially free from HMW and acidic variant obtained from step (f) onto Ceramic Hydroxy apatite (CHT) column;
- g. Optionally washing the CHT column with a suitable wash buffer;
- h. Eluting the protein of mixture from CHT column with suitable buffer;

wherein the eluted protein mixture is enriched with protein of interest and substantially free of impurities HMW, LMW's & basic variants (BV).

In an embodiment, the invention provides an anion exchange process to produce an antibody composition enriched antibody of interest and substantially reduced acidic variants and HMW or aggregates.

In an embodiment, the invention provides an anion exchange process performed in negative mode to produce an antibody composition enriched antibody of interest and substantially reduced acidic variants comprises about 14% or less AV, 13% or less AV, 12% or less AV, 11% or less AV, 10% or less AV, 9% or less AV, 8% or less AV, 7% or less AV, 6% or less AV, 5% or less AV, 4.5% or less AV, 4% or less AV, 3% or less AV, 2% or less AV, 1% or less AV.

In an embodiment, the invention provides an anion exchange process performed in negative mode to produce an antibody composition enriched antibody of interest and substantially reduced HMW comprises about 0.5% or less HMW. In one aspect of this embodiment, the low HMW composition comprises about 0.4% or less HMW, 0.3% or less HMW, 0.2% or less HMW, 0.1% or less HMW.

In an embodiment, the invention provides a CHT column chromatography process to produce an antibody composition enriched antibody of interest and reduced basic variants and LMW impurities.

In an embodiment, the invention provides the protein mixture eluted from CHT column comprises LMW selected from about 0.3% or less LMW, 0.2% or less LMW, 0.1% or less LMW analysed by SE-HPLC Analysis.

In an embodiment, the invention provides the protein mixture eluted from CHT column comprises LMW below 0.4%, analysed by SE-HPLC Analysis.

In an embodiment, the invention provides the protein mixture eluted from CHT column comprises low BV selected from about 14% or less BV, 13% or less BV, 12% or less BV, 11% or less BV, 10% or less BV, 9% or less BV, 8% or less BV, 7% or less BV, 6% or less BV, 5% or less BV, 4% or less BV, 3% or less BV, 2% or less BV, 1% or less BV.

In an embodiment, the invention provides the protein mixture eluted from CHT column comprises less than 10% BV.

In an embodiment, the invention provides the protein mixture eluted from CHT column comprises less than 5% BV.

In another embodiment, the invention provides a process of purifying the Omalizumab at 50 L scale or 200 L scale from protein mixture comprising:
- a. Obtaining protein mixture from the mammalian expression system comprising the protein of interest and at least one impurity selected from acidic variant, basic variant, low molecular weight (LMW), high molecular weight (HMW);
- b. Applying the protein mixture to affinity chromatography column;
- c. Eluting the protein mixture from affinity chromatography column;
- d. Performing the viral inactivation of the protein mixture obtained from step (c);
- e. Applying the protein mixture obtained from step (d) onto anion exchange chromatography;
- f. Eluting the protein mixture in flow through mode;
- g. Applying the protein mixture substantially free from HMW and acidic variant obtained from step (f) onto ceramic hydroxy apatite (CHT) column;
- h. Washing the CHT column with a suitable wash buffer;
- i. Eluting the protein of mixture from CHT column with suitable buffer wherein the eluted protein mixture is enriched with the Omalizumab and substantially free of impurities LMW's & basic variants (BV).

In an embodiment, the CHT washing removes loosely bound impurities.

In an embodiment, the invention provides an anion exchange process to produce Omalizumab composition enriched antibody of interest and substantially reduced acidic variants and HMW or aggregates.

In an embodiment, the invention provides an anion exchange process performed in negative mode to produce an antibody composition enriched the Omalizumab and substantially reduced acidic variants comprises about 14% or less AV, 13% or less AV, 12% or less AV, 11% or less AV, 10% or less AV, 9% or less AV, 8% or less AV, 7% or less AV, 6% or less AV, 5% or less AV, 4.5% or less AV, 4% or less AV, 3% or less AV, 2% or less AV, 1% or less AV.

In an embodiment, the invention provides an anion exchange process performed in negative mode to produce an antibody composition enriched the Omalizumab and substantially reduced HMW comprises about 0.5% or less HMW. In one aspect of this embodiment, the low HMW composition comprises about 0.4% or less HMW, 0.3% or less HMW, 0.2% or less HMW, 0.1% or less HMW analysed by SE-HPLC Analysis.

In an embodiment, the invention provides a CHT column chromatography process to produce an antibody composition enriched the Omalizumab and reduced basic variants and LMW impurities.

In an embodiment, the invention provides the protein mixture eluted from CHT column comprises LMW selected from about 0.3% or less LMW, 0.2% or less LMW, 0.1% or less LMW analysed by SE-HPLC Analysis.

In an embodiment, the invention provides the protein mixture eluted from CHT column comprises LMW below 0.4%, analysed by SE-HPLC Analysis.

In an embodiment, the invention provides the protein mixture eluted from CHT column comprises low BV selected from about 14% or less BV, 13% or less BV, 12% or less BV, 11% or less BV, 10% or less BV, 9% or less BV, 8% or less BV, 7% or less BV, 6% or less BV, 5% or less BV, 4% or less BV, 3% or less BV, 2% or less BV, 1% or less BV.

In an embodiment, the invention provides the protein mixture eluted from CHT column comprises less than 10% BV.

In an embodiment, the invention provides the protein mixture eluted from CHT column comprises less than 5% BV.

In an embodiment, the antibody is capable to bind IgE and thereby capable to treat allergic diseases, asthma, nasal polyps and urticaria. In preferred embodiment, the antibody is omalizumab.

In an embodiment, the purified pharmaceutical composition of biosimilar of Omalizumab comprising substantially purified monomer and impurity acidic variant less than 12%, basic variant less than 5%, LMW less than 0.4% and HMW less than 0.5%.

In an embodiment, antibodies are selected from IgG1, IgG2, IgG3, IgG4 and fusion proteins. In certain embodiments the antibodies are selected from Etanercept, Rituximab, Palivizumab, Infliximab, Trastuzumab, Alemtuzumab, Adalimumab, Ibritumomab tiuxetan, Omalizumab, Cetuximab, Bevacizumab, Natalizumab, Eculizumab, Certolizumab pegol, Ustekinumab, Canakinumab, Golimumab, Ofatumumab, Tocilizumab, Denosumab, Belimumab, Ipilimumab, Brentuximab vedotin, Pertuzumab, Trastuzumab emtansine, Raxibacumab, Obinutuzumab, Siltuximab, Ramucirumab, Vedolizumab, Blinatumomab, Nivolumab, Pembrolizumab, Darucizumab, Necitumumab, Dinutuximab, Secukinumab, Mepolizumab, Alirocumab, Evolocumab, Daratumumab, Elotuzumab, Ixekizumab, Reslizumab, Olaratumab, Bezlotoxumab, Atezolizumab, Obiltoxaximab, Sarilumab, Ocrelizumab, Tildrakizumab, Romosozumab, Brolucizumab, Crizanlizumab.

In an embodiment, the protein of interest is IgG1 antibody which binds to IgE. In preferred embodiment, the IgG1 antibody is biosimilar of Omalizumab.

In an embodiment, the chromatographic step performed in sequence after affinity chromatography are adjustable or replaceable with each other. In certain embodiment, CHT chromatography can be performed after affinity chromatography. In certain embodiment, CHT can be performed between affinity chromatography and AEX chromatography. In certain embodiment, CHT can be performed after affinity chromatography.

In certain embodiment, CHT can be performed between affinity chromatography and AEX chromatography.

Affinity Chromatography Conditions:

In an embodiment, wherein the affinity chromatography is selected from Protein A or Protein G. In an embodiment the affinity chromatography rein is selected from Mabselect, Mabselect SuRe, Mabselect SuRe LX, Prosep Ultra Plus, Eshmuno A. In preferred embodiment, the Affinity chromatography resin is Mabselect Sure LX.

In an embodiment, the equilibration buffer or loading buffer or wash buffer is selected from Sodium Phosphate, Tris-HCl, Tris-Acetate, HEPES, Glycine-NaOH.

In preferred embodiment, the loading buffer is Tris Acetate or Tris-HCl.

In certain embodiment, the equilibration buffer or loading buffer or wash buffer used in combination with a salt. In certain embodiment, the salt is selected from sodium Chloride, Potassium Chloride. In preferred embodiment, the salt is Sodium Chloride.

In an embodiment, the equilibration buffer has concentration range from about 5 mM to about 40 mM. In certain embodiment, the equilibration buffer has concentration range from about 10 mM to about 25 mM. In preferred embodiment, the equilibration buffer concentration is about 20 mM.

In certain embodiment, the equilibration buffer or loading buffer or wash buffer optionally comprises a salt selected from about 50 mM to about 400 mM. In an embodiment, the equilibration buffer comprises a salt buffer concentration selected from about 100 mM to about 200 mM. In an embodiment, the equilibration buffer concentration is about 150 mM. In another embodiment, the equilibration buffer concentration is about 100 mM.

In an embodiment, the equilibration buffer or loading buffer or wash buffer has conductivity range from about 10 mS/cm to about 20 mS/cm. In an embodiment, the equilibration buffer or loading buffer or wash buffer conductivity is about 15.0 mS/cm to 18.0 mS/cm. In another embodiment, the equilibration buffer or loading buffer or wash buffer conductivity is about 10.0 mS/cm to 13.0 mS/cm.

In an embodiment, the pH of the equilibration buffer or loading buffer or wash buffer is selected from about 6.5 to about 7.5. In preferred embodiment, the equilibration buffer pH is about 7.0.

In an embodiment, the loading buffer has concentration range from about 5 mM to about 40 mM. In an embodiment, the loading buffer has concentration range from about 10 mM to about 30 mM. In preferred embodiment, the loading buffer concentration is about 20 mM.

In certain embodiment, the affinity chromatography has at least one wash buffer. In another embodiment, the affinity chromatography has three wash buffers.

In an embodiment, the first wash buffer has concentration range from about 5 mM to about 40 mM.

In certain embodiment, the first wash buffer has concentration range from about 10 mM to about 25 mM. In preferred embodiment, the first wash buffer concentration is about 20 mM.

In an embodiment, the second wash buffer is selected from sodium phosphate, Tris-HCl, Tris-Acetate, HEPES, and Glycine-NaOH.

In certain embodiment, second wash buffer used in combination with a salt.

In certain embodiment, the salt is selected from sodium chloride, potassium Chloride. In preferred embodiment, the salt is Sodium Chloride.

In an embodiment, the second wash buffer has concentration range from about 5 mM to about 40 mM. In certain embodiment, the second wash buffer has concentration range from about 10 mM to about 25 mM. In preferred embodiment, the second wash buffer concentration is about 20 mM.

In an embodiment, the second wash buffer has a salt buffer concentration range from about 0.5 M to about 1.5 M. In preferred embodiment, the second wash buffer concentration is about 1.0 M.

In an embodiment, the second wash buffer has conductivity range from about 70 mS/cm to about 120 mS/cm. In an embodiment, the second wash buffer has conductivity range from about 80 mS/cm to about 100 mS/cm. In preferred embodiment, the second wash buffer conductivity is about 90 mS/cm.

In an embodiment, the pH of the second wash buffer is selected from about 6.5 to about 7.5. In preferred embodiment, the second wash buffer pH is about 7.0.

In an embodiment, the second wash buffer further comprises a surfactant which is selected from Polysorbate 20, Polysorbate 80, and Triton X-100, In an embodiment, the preferred surfactant is Polysorbate 20.

In an embodiment, the percentage of the surfactant in the second wash buffer is from about 0.01% to about 1%. In preferred embodiment, the surfactant in the second wash buffer is 0.1% (w/v).

In an embodiment, the third wash buffer has concentration range from about 5 mM to about 40 mM. In certain embodiment, the third wash buffer has concentration range from about 10 mM to about 30 mM. In preferred embodiment, the third wash buffer concentration is about 20 mM.

In an embodiment, the third wash buffer has concentration range from about 5 mM to about 40 mM. In certain embodiment, the third wash buffer has concentration range from about 10 mM to about 40 mM. In preferred embodiment, the third wash buffer concentration is about 30 mM.

In an embodiment, the third wash buffer has conductivity range from about 0.5 mS/cm to about 2.5 mS/cm. In preferred embodiment, the third wash buffer conductivity is less than 2.5 mS/cm.

In an embodiment, the pH of the third wash buffer is selected from about 5 to about 6. In preferred embodiment, the third wash buffer pH is about 5.5.

In an embodiment, the elution buffer is selected from Acetic acid, Phosphoric acid, Sodium acetate, and HCl. In preferred embodiment, the elution buffer is Acetic acid.

In an embodiment, the elution buffer is selected from Acetic acid, Phosphoric acid, Sodium acetate, and HCl. In preferred embodiment, the elution buffer is Sodium Acetate.

In an embodiment, the elution buffer has concentration range selected from about 25 mM to about 250 mM.

In an embodiment, the elution buffer has concentration range selected from about 100 mM to about 250 mM. In an embodiment, the elution buffer has a concentration range about 125 mM to 200 mM.

In an embodiment, the elution buffer has conductivity range from about 0.2 mS/cm to about 1.0 mS/cm. In an embodiment, the elution buffer has conductivity range from about 0.5 mS/cm to about 1.0 mS/cm. In an embodiment, the elution buffer has conductivity range from about 0.5 mS/cm to about 0.6 mS/cm. In an embodiment, the elution buffer has conductivity range from about 0.2 mS/cm to about 0.3 mS/cm.

In an embodiment, the pH of the elution buffer is selected from 2.5 to about 3.5. In preferred embodiment, the elution buffer pH is about 3.5.

In an embodiment, the elution buffer has conductivity range from about 0.2 mS/cm to about 0.3 mS/cm. In an embodiment, the pH of the elution buffer is selected from 2.5 to about 3.5. In preferred embodiment, the elution buffer pH is about 3.0.

In certain embodiment, elution is performed in linear gradient. In certain embodiment, the elution is performed in step gradient.

In an embodiment, where the elution peak Collection starts at an ascending value of about 2.5 AU/cm and ends at a descending value of about 2.5 AU/cm.

In an embodiment, where the elution peak Collection starts at an ascending value of about 0.25 AU/cm and ends at a descending value of about 0.25 AU/cm.

In an embodiment, the invention provides the antibody composition having a turbidity selected from less than about 100 NTU, less than about 50 NTU, less than about 30 NTU, less than about 10 NTU obtained from Affinity Chromatography wherein the elution buffer has a concentration of about 200 mM.

In another embodiment, the invention provides a purification process of antibodies or fragment thereof by using affinity chromatography wherein the elution is performed at low salt concentration.

In another embodiment, the invention provides a purification process of antibodies or fragment thereof by using affinity chromatography wherein the elution is performed at low salt concentration, which does not reduce the turbidity compared to elution performed with high salt concentration of the of the eluted protein mixture during viral inactivation.

In an embodiment, the equilibration is performed for about 3 CV's to about 10 CV's. In a preferred embodiment, the equilibration is performed for about 5 CV's. In an embodiment, the equilibration is performed until the equilibration buffer conductivity end point is achieved.

In an embodiment, the amount of protein loaded onto the column during loading is at a range of about 10 g/L to about 45 g/L. In an embodiment, the amount of protein loaded onto the column during loading is at a range from about 10 g/L to about 50 g/L.

In an embodiment, the first wash is performed for at least 1 to about 5 CV's. In preferred embodiment the first wash is performed for 3 CV's. In an embodiment, the first wash is performed until the buffer conductivity end point is achieved.

In an embodiment, the second wash is performed for at least 1CV to about 5 CV's. In preferred embodiment, the second wash is performed for 3 CV's. In an embodiment, the second wash is performed until the buffer conductivity end point is achieved.

In an embodiment, the third wash is performed for at least 4CV's to about 8 CV's. In preferred embodiment, the third wash is for 5 CV's. In an embodiment, the third wash is performed until the buffer conductivity end point is achieved.

In an embodiment, the residence time of the protein in the column during protein A purification has a range from about 2 minutes to about 6 minutes. In preferred embodiment, the residence time of the protein in the column is about 4 minutes.

AEX Chromatography Conditions:

In an embodiment, the anion exchange chromatography resin is selected from Capto Q, DEAE Sepharose fast flow, Fractogel EMD DEAE (M), Toyopearl DEAE-650, Q Sepharose Fast Flow, POROS XQ, POROS 50 HQ, POROS 50

PI, and POROS 50 D. In certain embodiment, the anion exchange chromatography resin is strong anion exchange POROS 50 HQ.

In an embodiment, the equilibration buffer or loading buffer is selected from Sodium Phosphate, Tris-HCl, HEPES, Glycine-NaOH, and Tris-Acetate. In certain embodiment, the equilibration buffer or loading buffer is Tris Acetate or Tris-HCl.

In an embodiment, the equilibration buffer has a concentration range from about 40 mM to about 60 mM. In a certain embodiment, the loading buffer concentration is about 50 mM. In a certain embodiment, the loading buffer concentration is about 20 mM.

In an embodiment, the equilibration buffer has conductivity range from about 1.5 mS/cm to about 3.5 mS/cm. In a certain embodiment, the equilibration buffer conductivity is less than 2.6 mS/cm.

In an embodiment, the pH of the equilibration buffer is selected from about 6.5 to about 7.5. In a certain embodiment, the loading buffer pH is about 7.0 to about 7.5. In an embodiment, the pH of loading buffer is 7.2-7.4.

In certain embodiment, the equilibration buffer conductivity is ≤2.0 mS/cm.

In an embodiment, the pH of the equilibration buffer is selected from about 6.5 to about 7.5.

In a certain embodiment, the loading buffer pH is about 7.0 to about 7.5. In an embodiment, the pH of loading buffer is 7.2-7.3.

In an embodiment, the loading buffer has a concentration range from about 40 mM to about 60 mM. In a certain embodiment, the loading buffer concentration is about 50 mM.

In an embodiment, the loading buffer has a concentration range from about 10 mM to about 30 mM. In a certain embodiment, the loading buffer concentration is about 20 mM.

In an embodiment, the loading buffer has conductivity range from about 1.5 mS/cm to about 3.5 mS/cm. In a certain embodiment, the loading buffer conductivity is less than 2.6 mS/cm.

In an embodiment, the pH of the loading buffer is selected from about 6.5 to about 7.5.

In certain embodiment, the loading buffer pH is about 7.0 to about 7.5. In an embodiment, the pH of loading buffer is 7.2-7.3.

In certain embodiment, the loading buffer conductivity is about ≤3.0 mS/cm.

In an embodiment, the pH of the loading buffer is selected from about 6.5 to about 7.5.

In certain embodiment, the loading buffer pH is about 7.0 to about 7.5. In an embodiment, the pH of loading buffer is 7.2-7.3.

In an embodiment, the invention provides protein peak collection criteria selected from the ascending value of about 2.5 AU/cm and ends at a descending value of about 1.5 AU/cm.

In an embodiment, the invention provides protein peak collection criteria selected from the ascending value of about 1.5 AU/cm and ends at a descending value of about 1.5 AU/cm.

In an embodiment, the invention provides the antibody composition comprising antibody of interest and about 10% to 12% acidic variant obtained from AEX chromatography wherein the peak collection criteria is selected from about 2.5 AU/cm to about 1.5 AU/cm.

In another embodiment, the invention provides protein peak collection criteria selected from the ascending value of about 1.5 AU/cm and ends at a descending value of about 1.5 AU/cm.

In an embodiment, the washing buffer is selected from sodium phosphate, Tris-HCl, HEPES, Glycine-NaOH, and Tris-Acetate.

In an embodiment, the washing buffer has concentration range from about 40 mM to about 60 mM. In certain embodiment, the washing buffer concentration is about 50 mM.

In another embodiment, the washing buffer has concentration range from about 10 to about 30 mM. In certain embodiment, the washing buffer concentration is about 20 mM.

In an embodiment, the washing buffer has conductivity range from about 1.5 mS/cm to about 3.5 mS/cm. In preferred embodiment, the washing buffer conductivity is less than 2.6 mS/cm.

In certain embodiment, the washing buffer conductivity is ≤2.0 mS/cm.

In an embodiment, the pH of the washing buffer is selected from about 6.5 to about 7.5. In certain embodiment the washing buffer pH is about 7.2.

In an embodiment, the regeneration buffer is selected from Sodium Phosphate, Tris-HCl, HEPES, Glycine-NaOH, Tris-Acetate.

In an embodiment, the regeneration buffer has concentration range from about 5 mM to about 30 mM. In certain embodiment, the regeneration buffer concentration is about 20 mM.

In an embodiment, the regeneration buffer also contains a salt selected from Sodium Chloride, Potassium Chloride, and Calcium Chloride. In certain embodiment, the salt in the regeneration buffer is Sodium Chloride.

In an embodiment, the salt in the regeneration buffer has concentration range from about 0.5M to about 1.5 M. In certain embodiment, the salt in the regeneration buffer has concentration of about 1.0 M.

In an embodiment, the regeneration buffer has conductivity range from about 80 mS/cm to about 90 mS/cm. In certain embodiment, the regeneration buffer conductivity is about 85 mS/cm.

In an embodiment, the regeneration buffer has conductivity range from about 90 mS/cm to about 110 mS/cm. In certain embodiment, the regeneration buffer conductivity is about 100 mS/cm.

In an embodiment, the pH of the regeneration buffer is selected from about 6.5 to about 7.5. In preferred embodiment, the regeneration buffer pH is about 7.0.

In an embodiment, the pH of the regeneration buffer is selected from about 6.5 to about 7.5. In preferred embodiment, the regeneration buffer pH is about 7.2.

In an embodiment, the elution is performed in a flow through mode.

In an embodiment, the sanitization buffer is selected from NaOH, Iso-propyl alcohol, benzyl alcohol. In certain embodiment, the sanitization buffer is NaOH.

In an embodiment, the sanitization buffer has concentration range from about 300 mM to about 1500 mM. In certain embodiment, the regeneration buffer concentration is about 500 mM.

In an embodiment, the loading is performed for at least about 5 CV's or more. In a certain embodiment the loading is performed for about 30 CV's.

In an embodiment, the equilibration is performed for at least about 3CV's to about 10 CV's. In a certain embodiment, the equilibration is performed for about 5 CV's.

In an embodiment, the equilibration is performed until the equilibration buffer conductivity end point is achieved.

In an embodiment, the amount of protein loaded onto the column during loading is selected from less than about 150 g/L, less than about 130 g/L, less than about 120 g/L, less than about 110 g/L, less than about 100 g/L.

In an embodiment, the washing is performed for at least about 5 CV's.

In an embodiment, the washing is performed for at least about 2 CV's.

In an embodiment, the regeneration is performed for at least 2 CV's to about 5 CV's. In a certain embodiment, the regeneration is performed for about 3 CV's.

In an embodiment, the regeneration removes most of the impurities. In preferred embodiment, the regeneration removes most of the HMWs, and acidic charged variant based impurities.

In an embodiment, the sanitization is performed for at least 2 CV's to about 5 CV's. In a certain embodiment, the sanitization is performed for about 3 CV's.

In an embodiment, the sanitization buffer is held in the column for about 15 minutes to about 60 minutes. In certain embodiment, the sanitization buffer is held in the column for about 20 minutes.

In an embodiment, the residence time of the protein in the column during AEX purification has a range from about 2 to about 6 minutes. In a certain embodiment, the residence time of the protein in the column is about 4 minutes.

Ceramic Hydroxy Apatite (CHT) Conditions:

In an embodiment, Ceramic Hydroxy apatite is CHT (Ceramic Hydroxy apatite) —Type 1 and CHT (Ceramic Hydroxy apatite) XT.

In an embodiment, the loading buffer, washing buffer, equilibration buffer and elution buffer is prepared by combining Buffer A and Buffer B.

In certain embodiment, buffer A is polar protic molecule. In certain embodiment, the polar protic molecule is selected from water (H—OH), acetic acid (CH3CO—OH) methanol (CH3-OH), ethanol (CH3CH2-OH), n-propanol (CH3CH2CH2-OH), n-butanol (CH3CH2CH2CH2-OH).

In preferred embodiment, wherein the polar protic molecule is water.

In an embodiment, buffer B is selected from Sodium Phosphate, Tris, HEPES, Glycine-NaOH. In preferred embodiment, the buffer B is Sodium Phosphate.

In an embodiment, the concentration range of buffer B is from about 20 mM to about 40 mM. In certain embodiment, the concentration of buffer B is about 32 mM.

In an embodiment, the concentration range of buffer B is from about 20 mM to about 40 mM. In certain embodiment, the concentration of buffer B is about 40 mM.

In an embodiment, the concentration range of equilibration buffer and loading buffer is from about 20 mM to about 40 mM. In certain embodiment, the concentration of equilibration buffer and loading buffer is about 32 mM.

In certain embodiment, the equilibration buffer, loading buffer and wash buffer are same in strength. In an embodiment, the strength of elution buffer is higher than loading buffer.

In an embodiment, the equilibration buffer and loading buffer has concentration range from about 20 to about 50 mM. In certain embodiment, the equilibration buffer concentration is about 40 mM.

In an embodiment, the equilibration buffer has a concentration from about 20 mM to 50 mM. In certain embodiment, the equilibration buffer has a concentration of about 32 mM.

In an embodiment, the pH of the equilibration buffer or loading buffer or washing buffer or elution buffer is selected from about 6.5 to about 7.5.

In an embodiment, wherein the buffer pH is about 7.0±0.2.

In an embodiment, the equilibration buffer has conductivity range from about 3.0 to about 7.0 mS/cm. In preferred embodiment, the equilibration buffer conductivity is about 6.0 mS/cm.

In an embodiment, the pH of the equilibration buffer is selected from about 6.5 to about 7.5.

In an embodiment, the equilibration buffer pH is about 7.0±0.2.

In an embodiment, the equilibration is performed with isocratic gradient by using combination of at least two buffers where buffer A concentration is at least 10% of buffer B concentration. In preferred embodiment, buffer A concentration is at least 8% of buffer B concentration.

In an embodiment, the loading buffer has concentration range from about 30 to about 60 mM. In preferred embodiment, the loading buffer concentration is about 40 mM.

In an embodiment, the loading buffer has a concentration from about 10 mM to 40 mM. In certain embodiment, the loading buffer has a concentration of about 32 mM.

In an embodiment, the loading buffer has conductivity range from about 3.0 to about 7.0 mS/cm.

In preferred embodiment, the loading buffer conductivity is about 6.0 mS/cm.

In an embodiment, the pH of loading buffer is selected from about 6.5 to about 7.5.

In an embodiment, the loading buffer pH is about 7.0±0.2.

In an embodiment, the loading is performed with isocratic gradient by using combination of at least two buffers where buffer A concentration is at least 10% of buffer B concentration. In preferred embodiment, buffer A concentration is at least 8% of buffer B.

In an embodiment, the washing buffer has concentration range from about 30 mM to about 60 mM. In preferred embodiment, the washing buffer concentration is about 40 mM.

In an embodiment, the washing buffer has a concentration from about 10 mM to 40 mM. In certain embodiment, the washing buffer has a concentration of about 32 mM.

In an embodiment, the washing buffer has conductivity range from about 3.0 mS/cm to about 7.0 mS/cm. In preferred embodiment, the washing buffer conductivity is about 6.0 mS/cm.

In an embodiment, the pH of the washing buffer is selected from about 6.5 to about 7.5.

In an embodiment, wherein the washing buffer pH is about 7.0±0.2.

In an embodiment, the washing is performed with isocratic gradient by using combination of at least two buffers where buffer A concentration is at least 10% of, buffer B or less. In preferred embodiment, buffer A concentration is at least 10% of, buffer B concentration.

In an embodiment, the elution buffer has concentration range from about 10 mM to about 400 mM. In preferred embodiment, the elution buffer has a concentration range from about 32 mM to about 104 mM.

In an embodiment, the elution buffer has concentration range from about 10 mM to about 400 mM. In preferred embodiment, the elution buffer has a concentration range from about 24 mM to about 100 mM.

In an embodiment, the elution buffer has concentration range from about 10 mM to about 400 mM.

In preferred embodiment, the elution buffer has a concentration range from about 32 mM to about 88 mM.

In an embodiment, the elution buffer has concentration range from about 10 mM to about 400 mM. In preferred embodiment, the elution buffer has a concentration range from about 40 mM to about 96 mM.

In an embodiment, the elution buffer has conductivity range from about 6 mS/cm to about 12 mS/cm.

In an embodiment the pH of the elution buffer is selected from about 6.5 to about 7.5. In an embodiment, the elution buffer pH is about 7.0±0.2.

In an embodiment, the elution is performed in linear gradient. In certain embodiment, the elution is performed in step gradient.

In an embodiment, the elution is performed with linear gradient by using combination of at least two buffers wherein buffer A concentration is at least 10% of buffer B concentration. In such embodiment, buffer A concentration is at least 10% of buffer B concentration. In such embodiment, buffer B is gradually increased from about 10% to about 24% and optimized concentration of buffer B accordingly.

Moreover, any skilled person will appreciate the minor changes in gradient with respect to run time and particular impurity to be removed.

In such embodiment, elution is performed in isocratic gradient with 15% of buffer B. In such embodiment, elution is performed in isocratic gradient with 20% of buffer B. In such embodiment, elution is performed in isocratic gradient with 15%, 16%, 17%, 18%, 19%, 20% of buffer B.

In another embodiment, the elution is performed with linear gradient by using combination of at least two buffers wherein buffer A concentration is at least 8% of buffer B concentration. In such embodiment, buffer A concentration is at least 8 of, buffer B % concentration. In such embodiment, buffer B is gradually increased from about 8% to about 22% and optimized concentration of buffer B accordingly.

In an embodiment, wherein the elution peak collection starts at an ascending value of about 1.5 AU/cm and ends at a descending value of about 2.0 AU/cm for minimising LMWs.

In an embodiment, wherein the elution peak collection starts at an ascending value of about 1.0 AU/cm and ends at a descending value of about 1.5 AU/cm for minimising LMWs.

In certain embodiment, the CHT is performed in bind and elute mode.

In certain embodiment, the CHT is performed with buffer or solvent free from calcium chloride.

In certain embodiment, the concentration of the elution buffer is higher than wash buffer.

In an embodiment, the elution buffer comprises at least 8% the concentration of the 400 mM salt buffer. In an embodiment, the elution buffer comprises at least 10% the concentration of the 400 mM salt buffer. In an embodiment, the elution buffer comprises at least 15% the concentration of the 400 mM salt buffer. In an embodiment, the elution buffer comprises at least 20% the concentration of the 400 mM salt buffer. In an embodiment, the elution buffer comprises at least 26% the concentration of the 400 mM salt buffer.

In an embodiment, the elution is performed for about 5 CV's to about 10 CV's.

In an embodiment, the elution is performed for about 10 CV's to about 15 CV's.

In an embodiment, the elution is performed for about 15 to about 20 CV's or more. In a preferred embodiment, the elution takes place for about 19 CV's.

In an embodiment, the equilibration is performed for about 3 CV's to about 10 CV's. In a preferred embodiment, the equilibration takes place for about 5 CV's.

In an embodiment, the equilibration is performed until the equilibration buffer conductivity end point is achieved.

In an embodiment, the amount of protein loaded onto the column during loading is in the range from about 5 g/L to about 25 g/L. In an embodiment, amount of protein loaded onto the column during loading is 12.5 g/L.

In an embodiment, the washing is performed for at least about 2 CV's to about 5 CV's. In preferred embodiment, the washing is performed for about 3 CV's. In an embodiment, the washing is performed until the buffer conductivity end point is achieved.

In an embodiment, the residence time of the protein in the CHT column during equilibration washing and loading is in the range from about 2 minutes to about 6 minutes. In preferred embodiment, the residence time of the protein in the column during equilibration, washing and loading is about 4 minutes.

In an embodiment, the residence time of the protein in the column during elution has a range from about 2 minutes to about 6 minutes. In preferred embodiment, the residence time of the protein in the column during elution is about 4 minutes.

The present invention provides below examples for illustrative purpose only and invention should not be considered limiting to below examples.

Example 1—Purification of Monoclonal Antibody by Performing Affinity Column Followed by Anion Exchange Column All chromatographic processes were carried out using an AKTA Pure 150 system from GE Healthcare. Concentration of protein samples were determined by measuring absorbance at 280 nm using Shimadzu Spectrophotometer. Mabselect Sure LX resin media obtained from GE Healthcare. Vantage columns and C 10/20 columns were obtained from Millipore Corporation and GE Healthcare respectively. Turbidity measurements were measured using from Thermo scientific. All Chemicals were obtained from JTB or Merck Millipore and were of GMP grade.

A monoclonal antibody molecule capable to bind to IgE molecule expressed in Chinese Hamster Ovary (CHO) cell line is captured using Protein A (Mab Select Sure LX, GE Healthcare) packed in VL 11/250 or C10/20 column. The residence time is 4 min for all the phases. After equilibration with Tris Acetate+100 mM NaCl, pH 6.8-7.2 clarified harvest is loaded at ≤45 mg/ml of the resin. After loading, the column is washed with equilibration buffer (wash 1) followed by wash 2 and wash 3 buffer as mentioned in Table 1. Affinity chromatography step is operated in bind and eluate mode and collection is done from 50 mAU (0.25 AU/cm) ascending to 50 mAU (0.25 AU/cm) descending of the peak. Protein A output is analysed with SE-HPLC, CEX-HPLC for size and charge variants. The experimental design for Protein A step is summarized in Table 1.

TABLE 1

| | | Residence Time (min) | Column Volume (CV) |
|---|---|---|---|
| Step | Buffer | | |
| WFI | WFI | 4 | 2-3 |
| Sanitization | 0.1M NaOH | 4 | 2-3 |
| Equilibration | 20 mM Tris-acetate + 100 mM NaCl, pH 7.0 ± 0.2 | 4 | 5 |
| Load | Clarified Harvest | 4 | Till loading volume |
| Wash 1 | 20 mM Tris-acetate + 100 mM NaCl, pH 7.0 ± 0.2 | 4 | 3 or till conductivity achieved |
| Wash 2 | 20 mM Tris-acetate + 1M NaCl, pH 7.0 ± 0.2 | 4 | 3 or till conductivity achieved |
| Wash 3 | 20 mM Tris-acetate, pH 5.5 ± 0.2 | 4 | 5-6 |
| Elution | 200 mM Acetic acid, pH 3.0 ± 0.1 | 4 | 3 |
| Neutralization wash | 20 mM Tris-acetate + 100 mM NaCl, pH 7.0 ± 0.2 | 4 | 3 |
| Sanitization | 0.1M NaOH | 4 | 2-3 |
| Neutralization wash | 20 mM Tris-acetate + 100 mM NaCl, pH 7.0 ± 0.2 | 4 | 5 |
| Storage | 2% Benzyl alcohol in Wash 3 buffer | 4 | 2-3 |

*Experimental design for Protein A*

Eluted protein is further subjected to viral inactivation and neutralization. After neutralization, protein has been filtered by 0.2 μm filter.

Post viral inactivation and neutralization step, the eluted protein mixture is further purified using Anion Exchange Chromatography resin (Poros HQ, Thermofisher) packed in C10/20 column.

The residence time is 4 min for all the phases. After equilibration with Tris Acetate, pH 7.0-7.3 Neutralized Protein A output is loaded at ≤100 mg/mL of the resin. The Load is diluted with water to meet the (mS/cm) conductivity specification i. e. ≤3.0 mS/cm before introducing it into the AEX column.

AEX step is operated in Flow-through (negative) mode and collection is done from 500 mAU ascending to 300 mAU descending of the peak. The column is washed using Tris Acetate, pH 7.0-7.3. AEX output is analysed with SE-HPLC, CEX-HPLC for size and charge variants. The experimental design for POROS 50 HQ step is summarized in Table 2.

TABLE 2

| | | Residence Time (min) | Column Volume (CV) |
|---|---|---|---|
| Step | Buffer | | |
| Sanitization | 0.5N Sodium Hydroxide | 4 | 2-3 CV |
| Equilibration | 50 mM Tris Acetate, pH 7.2-7.3 | 4 | 3-4 CV |
| Load | 50 mM Tris Acetate, pH 7.2-7.3 | 4 | Till loading volume |
| Wash | 50 mM Tris Acetate, pH 7.2-7.3 | 4 | Till absorbance 1.5 AU/cm |
| Sanitization | 0.5N Sodium Hydroxide | 4 | 2-3 CV |
| Storage | 0.1N Sodium Hydroxide | 4 | 2-3 CV |

*Experimental design for POROS 50 HQ (AEX)*

TABLE 3

SE (Size Exclusion)-HPLC (High performance Liquid Chromatography Analysis) SE-HPLC Analysis

| Sample | Main Peak Purity (%) | HMW (%) |
|---|---|---|
| AEX IP | 94.62 | 4.71 |
| AEX OP | 99.34 | 0.07 |

Table 3 shows 99% purity of main peak and 98% reduction of HMW which is determined by SE-HPLC.

CEX-HPLC Analysis

| Sample | Main Peak + K1 + K2 (%) | Acidic Variants (%) |
|---|---|---|
| NPEL/AEX IP | 65.86 | 18.28 |
| AEX OP | 74.11 | 8.24 |

Table 4 shows 74% % purity of main peak and approximately 55% reduction of acidic variants which is determined by CEX-HPLC.

Example 2—Purification of Monoclonal Antibody by Performing Affinity Chromatography Followed by AEX Chromatography Followed by CHT Type 1 Resin All chromatographic processes were carried out using an AKTA Pure 150 system from GE Healthcare. Concentration of protein samples were determined by measuring absorbance at 280 nm using Shimadzu Spectrophotometer. CHT Type I resin media obtained from Bio-rad. Vantage columns and C 10/20 columns were obtained from Millipore Corporation and GE Healthcare respectively. Turbidity measurements were measured using from Thermo scientific. All Chemicals were obtained from JTB or Merck Millipore and were of GMP grade.

A monoclonal antibody capable to bind to IgE expressed in Chinese Hamster Ovary (CHO) cell line is captured using Protein A (Mab Select Sure LX, GE Healthcare) packed in VL 11/250 column. Eluted protein is further subjected to viral inactivation and neutralization. After neutralization, protein has been filtered by 0.2 μm filter.

Post viral inactivation and neutralization step, the protein mixture is further purified using Anion Exchange Chromatography resin (Poros HQ, Thermofisher) packed in C10/20 column.

Eluted protein from Anion Exchange Chromatography (AEX) is further polished using mixed-mode resin (CHT Type I, Bio-rad) packed in VL 11/250 column. The residence time is 4 min/3 min for all the phases. After equilibration with Na Phosphate, pH 6.8 Anion exchange (AEX) output is loaded at 12.5 mg/mL of the resin. The column is washed using 3 CV, Na Phosphate, pH 6.8. Bound protein of interest is eluted using linear gradient between 32 mM Na Phosphate and 400 mM Na Phosphate, pH 6.8. Eluted peak of interest is analysed with SE-HPLC, CEX-HPLC for size and charge variants. The experimental design and process for CHT Type I step is summarized in Table 5.

TABLE 5

| | | Residence Time (min) | Column Volume (CV) |
|---|---|---|---|
| Step | Buffer | | |
| Sanitization | 0.5N Sodium Hydroxide | 4 | 3 CV and 0.5 hr hold |
| Charge | 400 mM Na Phosphate, pH 6.8 | 4 | 3 CV |
| Equilibration | 32 mM Na Phosphate, pH 6.8 | 4 | 3 CV or conductivity end point |
| Load | AEX Eluate + 32 mM Na Phosphate, pH 6.8 | 4 | Till loading volume |
| Wash | 32 mM Na Phosphate, pH 6.8 | 4 | 3 CV |
| Gradient Elution | Buffer A: Water Buffer B: 400 mM Phosphate, pH 6.8 from 8 % to 22% B | 3 to 4 | 19 CV |
| Strip | 400 mM Phosphate, pH 6.8 | 3 to 4 | 3 CV |
| Sanitization | 0.5N Sodium Hydroxide | 3 to 4 | 3 CV and 0.5 hr hold |
| Storage | 0.1N Sodium Hydroxide | 3 to 4 | 3 CV |

Example 3—Purification of Monoclonal Antibody by Performing Affinity Chromatography Followed by AEX Chromatography Followed by CHT XT Resin

All chromatographic processes were carried out using an AKTA Pure 150 system from GE Healthcare. Concentration of protein samples were determined by measuring absorbance at 280 nm using Shimadzu Spectrophotometer. CHT XT resin media obtained from Bio-rad. Vantage columns and C 10/20 columns were obtained from Millipore Corporation and GE Healthcare respectively. Turbidity measurements were measured using from Thermo scientific. All Chemicals were obtained from JTB or Merck Millipore and were of GMP grade.

A monoclonal antibody capable to bind to IgE expressed in Chinese Hamster Ovary (CHO) cell line is captured using Protein A (Mab Select Sure LX, GE Healthcare) packed in VL 11/250 column.

Eluted protein is further subjected to viral inactivation and neutralization. After neutralization, protein has been filtered by 0.2 μm filter.

Post viral inactivation and neutralization step, the eluted protein mixture is further purified using Anion Exchange Chromatography resin (Poros HQ, Thermofisher) packed in C10/20 column.

Eluted protein from Anion Exchange Chromatography (AEX) is further polished using mixed-mode resin (CHT XT, Bio-rad) packed in VL 11/250 column. The residence time is 4 min/3 min for all the phases. After equilibration with Na Phosphate, pH 6.8 Anion exchange (AEX) output is loaded at 12.5 mg/mL of the resin. The column is washed using 3 CV, Na Phosphate, pH 6.8. Bound protein of interest is eluted using linear gradient between 40 mM Na Phosphate and 400 mM Na Phosphate, pH 6.8. Eluted peak of interest is analysed with SE-HPLC, CEX-HPLC for size and charge variants. The experimental design and process for CHT XT step is summarized in Table 6-9.

TABLE 6

| | | Residence Time (min) | Column Volume (CV) |
|---|---|---|---|
| Step | Buffer | | |
| Sanitization | 0.5N Sodium Hydroxide | 4 | 3 CV and 0.5 hr hold |
| Charge | 400 mM Na Phosphate, pH 6.8 | 4 | 3 CV |
| Equilibration | 40 mM Na Phosphate, pH 6.8 | 4 | 3 CV or conductivity end point |
| Load | AEX Eluate + 40 mM Na Phosphate, pH 6.8 | 4 | Till loading volume |
| Wash | 40 mM Na Phosphate, pH 6.8 | 4 | 2-3 CV |
| Gradient Elution | Buffer A: Water Buffer B: 400 mM Phosphate, pH 6.8 from 10% to 24% B | 3 to 4 | 19 CV |
| Strip | 400 mM Phosphate, pH 6.8 | 3 to 4 | 3 CV |
| Sanitization | 0.5N Sodium Hydroxide | 3 to 4 | 3 CV and 0.5 hr hold |
| Storage | 0.1N Sodium Hydroxide | 3 to 4 | 3 CV |

TABLE 7

SE-HPLC Analysis of Eluate of CHT Type I/XT Column

| Process output | Main Peak (%) | LMW (%) |
|---|---|---|
| NPEL | 94.55 | 0.84 |
| AEX OP | 99.31 | 0.67 |
| CHT Type EXT OP | 99.99 | 0.00 |

It is evident from the data that composition obtained from CHT has substantially reduced approx. 100% LMW and purity of protein is 99.99% by SE-HPLC.

TABLE 8

Size related Varients: CE-SDS

| Process output | Total LMW (%) |
|---|---|
| NPEL | 8.91 |
| AEX OP | 7.48 |
| CHT Type EXT OP | 1.42 |

It is evident from the data that composition obtained from CHT has substantially reduced approx. 81% LMW.

TABLE 9

Charge related Variants: CEX-HPLC

| Process output | Main Peak (%) | Basic (%) |
|---|---|---|
| NPEL | 73.38 | 12.83 |
| AEX OP | 77.33 | 12.19 |
| CHT Type I/XT OP | 84.72 | 5.27 |

Table 9 shows 84% purity of main peak and approximately 56% reduction of LMW which is determined by CEX-HPLC.

Example 4—Purification of Monoclonal Antibody by Performing Affinity Column Followed by Anion Exchange Column (50 L Scale)

All chromatographic processes were carried out using an AKTA Pilot or AKTA Process from GE Healthcare. Concentration of protein samples were determined by measuring absorbance at 280 nm using Spectrophotometer. Mabselect Sure LX resin media obtained from GE Healthcare. Chromatographic 100/250 columns were obtained from Millipore Corporation or GE Healthcare or Repligen. All Chemicals used during manufacturing process were of GMP grade.

A monoclonal antibody molecule capable to bind to IgE molecule expressed in Chinese Hamster Ovary (CHO) cell line is captured using Protein A (Mab Select Sure LX, GE Healthcare) packed in Chromatographic 100/250 column. The residence time is 4 min for all the phases. After equilibration with Tris HCl+150 mM NaCl, pH 6.8-7.2 clarified harvest is loaded at ≤45 mg/mL of the resin. After loading column is washes with equilibration buffer (wash 1) followed by wash 2 and wash 3 buffer as mentioned in Table 10. Affinity chromatography step is operated in bind and eluate mode and collection is done from 0.25 AU/cm ascending to 0.25 AU/cm descending of the peak. Protein A output is analysed with SE-HPLC, CEX-HPLC for size and charge variants. The experimental design for Protein A step is summarized in Table 10.

TABLE 10

Experimental design for Protein A

| Step | Buffer | Residence Time (min) | Column Volume (CV) |
|---|---|---|---|
| Sanitization | 0.1M NaOH | 4 | 2-3 |
| Equilibration | 20 mM Tris-HCl + 150 mM NaCl, pH 7.0 ± 0.2 | 4 | 5 or to pH end point |
| Load | Clarified Harvest | 4 | Till loading volume |
| Wash 1 | 20 mM Tris-HCl + 150 mM NaCl, pH 7.0 ± 0.2 | 4 | 3 |
| Wash 2 | 20 mM Tris-HCl + 1M NaCl, pH 7.0 ± 0.2 | 4 | 5 |
| Wash 3 | 30 mM Sodium acetate, pH 5.5 ± 0.2 | 4 | 7 |
| Elution | 200 mM Sodium acetate, pH 3.5 ± 0.1 | 4 | 5 |
| Strip | 100 mM Acetic acid | 4 | 3 |
| Equilibration | 20 mM Tris-HCl + 150 mM NaCl, pH 7.0 ± 0.2 | 4 | 3 |
| Sanitization | 0.1M NaOH | 4 | 3 |
| Equilibration | 20 mM Tris-HCl + 150 mM NaCl, pH 7.0 ± 0.2 | 4 | 5 or to pH end point |
| Storage | 20% Ethanol | 4 | 3 |

Eluted protein is further purified using Anion Exchange Chromatography resin (POROS 50 HQ, Thermofisher) packed in Chromatographic 100/250 column. The residence time is 4 min for all the phases. After equilibration with Tris HCl, pH 7.1-7.3 Neutralized Protein A output is loaded at 70 to 145 mg/mL of the resin. The Load is diluted with water to meet the (mS/cm) conductivity specification i. e. ≤2.0 mS/cm before introducing it into the AEX column.

AEX step is operated in Flow-through (negative) mode and collection is done from 2.0 AU/cm ascending to 2.5 AU/cm descending of the peak. The column is washed using Tris HCl, pH 7.1-7.3. AEX output is analysed with SE-HPLC, CEX-HPLC for size and charge variants. The experimental design for POROS 50 HQ step is summarized in Table 11.

TABLE 11

Experimental design for AEX

| Step | Buffer | Residence Time (min) | Column Volume (CV) |
|---|---|---|---|
| Sanitization | 0.5N Sodium Hydroxide | 4 | 3 CV |
| Charge | 20 mM Tris HCl, 1M NaCl pH 7.2 | 4 | 5 CV or pH end point |
| Equilibration | 20 mM Tris HCl, pH 7.2 | 4 | 5 CV or pH end point |
| Load | AEX Load pH 7.2 conductivity ≤ 2.0 mS/cm | 4 | Till loading volume |
| Chase | 20 mM Tris HCl, pH 7.2 | 4 | 3 CV |
| Strip | 20 mM Tris HCl, 1M NaCl pH 7.2 | 4 | 3 CV |
| Sanitization | 0.5N Sodium Hydroxide | 4 | 3 CV |
| Storage | 0.1N Sodium Hydroxide | 4 | 3 CV |

TABLE 12

SE (Size Exclusion)-HPLC (High performance Liquid Chromatography Analysis)
SE-HPLC Analysis

| Sample | Main Peak Purity (%) | HMW (%) |
|---|---|---|
| AEX IP | 95.52 | 3.80 |
| AEX OP | 99.45 | 0.14 |

Table 12 shows 99% purity of main peak and 96% reduction of HMW which is determined by SE-HPLC.

Table 13: shows the results of Cation Exchange—High performance Liquid Chromatography comparing the main peak with acidic variants.

TABLE 13 shows the results of Cation Exchange - High performance Liquid Chromatography comparing the main peak with acidic variants.
CEX-HPLC Analysis

| Sample | Main Peak (%) | Acidic Variants (%) |
|---|---|---|
| NPEL/AEX IP | 66.53 | 15.80 |
| AEX OP | 67.47 | 11.78 |

Table 13 shows 67% purity of main peak and approximately 25% reduction of acidic variants which is determined by CEX-HPLC.

Example 5—Purification of Monoclonal Antibody by Performing Affinity Chromatography Followed by AEX Chromatography Followed by CHT XT Resin All chromatographic processes were carried out using an AKTA Pilot or AKTA Process system from GE Healthcare.

Concentration of protein samples were determined by measuring absorbance at 280 nm using Spectrophotometer. CHT XT resin media obtained from Bio-rad. Chromatographic 100/250 columns were obtained from Millipore Corporation or GE Healthcare or Repligen. All Chemicals used during manufacturing process were of GMP grade.

A monoclonal antibody capable to bind to IgE expressed in Chinese Hamster Ovary (CHO) cell line is captured using Protein A (Mab Select Sure LX, GE Healthcare) packed in Chromatographic 100/250 column. Eluted protein is further subjected to viral inactivation and neutralization followed by depth filtration. After depth filtration, protein has been filtered by 0.2 μm filter.

Post depth filtration step, the protein mixture is further purified using Anion Exchange Chromatography resin (Poros HQ, Thermofisher) packed in Chromatographic 100/250 column.

Eluted protein from Anion Exchange Chromatography (AEX) is further polished using mixed-mode resin (CHT XT, Bio-rad) packed in Chromatographic 100/250 column. The residence time is 4 min/5 min for all the phases. After equilibration with Na Phosphate, pH 6.8 Anion exchange (AEX) output is loaded at maximum of 12.5 mg/mL of the resin. The column is washed using 3 CV, Na Phosphate, pH 6.8. Bound protein of interest is eluted using linear gradient between 40 mM Na Phosphate and 400 mM Na Phosphate, pH 6.8. Eluted peak of interest is analysed with SE-HPLC, CEX-HPLC for size and charge variants. The experimental design and process for CHT XT step is summarized in Table 14-17.

TABLE 14-continued

Experimental design for CHT XT

| Step | Buffer | Residence Time (min) | Column Volume (CV) |
|---|---|---|---|
| Strip | 400 mM Phosphate, pH 6.8 | 4 to 5 | 3 CV |
| Sanitization | 0.5N Sodium Hydroxide | 4 to 5 | 3 CV and 0.5 hr hold |
| Storage | 0.1N Sodium Hydroxide | 4 to 5 | 3 CV |

TABLE 15

SE HPLC analysis of LMW
SE-HPLC Analysis

| Sample | Main Peak Purity (%) | (%) LMW Variants |
|---|---|---|
| CHT IP | 99.45 | 0.40 |
| CHT OP | 99.94 | 0.02 |

TABLE 16

CEX HPLC-BV analysis
CEX-HPLC Analysis

| Sample | Main Peak Purity (%) | (%) Basic Variants |
|---|---|---|
| CHT IP | 67.47 | 11.40 |
| CHT OP | 74.74 | 3.96 |

TABLE 17

Analysis of LMWs by CE-SDS

| | % LMW | | | | | | | |
|---|---|---|---|---|---|---|---|---|
| DSP Step | 8 LC ~23.9 kDa | 7 NA NA | 6 HC ~50.7 kDa | 5 HH ~101.4 kDa | 4 HH ~101.4 kDa | 3 2H1L ~125.3 kDa | Total of LMW NA NA | Main Peak Main peak ~149.2 kDa |
| AEX Pool | 0.46 | 0 | 0.3 | 0.05 | 0.16 | 2.47 | 3.82 | 96.20 |
| CHT Eluate (Pool) | 0.32 | 0 | 0.16 | 0.04 | 0.08 | 1.32 | 2.26 | 97.74 |

TABLE 14

Experimental design for CHT XT

| Step | Buffer | Residence Time (min) | Column Volume (CV) |
|---|---|---|---|
| Sanitization | 0.5N Sodium Hydroxide | 4 to 5 | 3 CV and 0.5 hr hold |
| Charge | 400 mM Na Phosphate, pH 6.8 | 4 to 5 | 3 CV |
| Equilibration | 40 mM Na Phosphate, pH 6.8 | 4 to 5 | 3 CV or conductivity end point |
| Load | AEX Eluate + 40 mM Na Phosphate, pH 6.8 | 4 to 5 | Till loading volume |
| Wash | 40 mM Na Phosphate, pH 6.8 | 4 to 5 | 3 CV |
| Gradient Elution | BufferA: Water Buffer B: 400 mM Phosphate, pH 6.8 from 10% to 24% B | 4 to 5 | 19 CV |

Result: Table shows total reduction of LMWs by 40%.

Example 6—Purification of Monoclonal Antibody by Performing Affinity Column Followed by Anion Exchange Column (200 L Scale)

All chromatographic processes were carried out using an AKTA Pilot or AKTA Process from GE Healthcare. Concentration of protein samples were determined by measuring absorbance at 280 nm using Spectrophotometer. Mabselect Sure LX resin media obtained from GE Healthcare. Chromatographic 250/250 columns were obtained from Millipore Corporation or GE Healthcare or Repligen. All Chemicals used during manufacturing process were of GMP grade.

A monoclonal antibody molecule capable to bind to IgE molecule expressed in Chinese Hamster Ovary (CHO) cell line is captured using Protein A (Mab Select Sure LX, GE Healthcare) packed in Chromatographic 250/250 column. The residence time is 4 min for all the phases. After equilibration with Tris HCl+150 mM NaCl, pH 6.8-7.2 clarified harvest is loaded at ≤45 mg/mL of the resin. After loading column is washes with equilibration buffer (wash 1) followed by wash 2 and wash 3 buffer as mentioned in Table 18. Affinity chromatography step is operated in bind and eluate mode and collection is done from 0.25 AU/cm ascending to 0.25 AU/cm descending of the peak. Protein A output is analysed with SE-HPLC, CEX-HPLC for size and charge variants. The experimental design for Protein A step is summarized in Table 18.

TABLE 18

| | Experimental design for Protein A | | |
|---|---|---|---|
| Step | Buffer | Residence Time (min) | Column Volume (CV) |
| Sanitization | 0.1M NaOH | 4 | 2-3 |
| Equilibration | 20 mM Tris-HCl + 150 mM NaCl, pH 7.0 ± 0.2 | 4 | 5 or to pH end point |
| Load | Clarified Harvest | 4 | Till loading volume |
| Wash 1 | 20 mM Tris-HCl + 150 mM NaCl, pH 7.0 ± 0.2 | 4 | 3 |
| Wash 2 | 20 mM Tris-HCl + 1M NaCl, pH 7.0 ± 0.2 | 4 | 5 |
| Wash 3 | 30 mM Sodium acetate, pH 5.5 ± 0.2 | 4 | 7 |
| Elution | 200 mM Sodium acetate, pH 3.5 ± 0.1 | 4 | 5 |
| Strip | 100 mM Acetic acid | 4 | 3 |
| Equilibration | 20 mM Tris-HCl + 150 mM NaCl, pH 7.0 ± 0.2 | 4 | 3 |
| Sanitization | 0.1M NaOH | 4 | 3 |
| Equilibration | 20 mM Tris-HCl + 150 mM NaCl, pH 7.0 ± 0.2 | 4 | 5 or to pH end point |
| Storage | 20% Ethanol | 4 | 3 |

Eluted protein is further purified using Anion Exchange Chromatography resin (POROS 50 HQ, Thermofisher) packed in Chromatographic 350/250 or 200/350 column. The residence time is 4 min for all the phases. After equilibration with Tris HCl, pH 7.1-7.3 Neutralized Protein A output is loaded at 70 to 145 mg/mL of the resin. The Load is diluted with water to meet the (mS/cm) conductivity specification i. e. ≤2.0 mS/cm before introducing it into the AEX column.

AEX step is operated in Flow-through (negative) mode and collection is done from 2.0 AU/cm ascending to 2.5 AU/cm descending of the peak. The column is washed using Tris HCl, pH 7.1-7.3. AEX output is analysed with SE-HPLC. CEX-HPLC for size and charge variants. The experimental design for POROS 50 HQ step is summarized in Table 19.

TABLE 19

| | Experimental design for AEX: | | |
|---|---|---|---|
| Step | Buffer | Residence Time (min) | Column Volume (CV) |
| Sanitization | 0.5N Sodium Hydroxide | 4 | 3 CV |
| Charge | 20 mM Tris HCl, 1M NaCl pH 7.2 | 4 | 5 CV or pH end point |
| Equilibration | 20 mM Tris HCl, pH 7.2 | 4 | 5 CV or pH end point |
| Load | AEX Load pH 7.2 conductivity ≤ 2.0 mS/cm | 4 | Till loading volume |

TABLE 19-continued

| | Experimental design for AEX: | | |
|---|---|---|---|
| Step | Buffer | Residence Time (min) | Column Volume (CV) |
| Chase | 20 mM Tris HCl, pH 7.2 | 4 | 3 CV |
| Strip | 20 mM Tris HCl, 1M NaCl pH 7.2 | 4 | 3 CV |
| Sanitization | 0.5N Sodium Hydroxide | 4 | 3 CV |
| Storage | 0.1N Sodium Hydroxide | 4 | 3 CV |

TABLE 20

| SE (Size Exclusion)-HPLC (High performance Liquid Chromatography Analysis) SE-HPLC Analysis | | |
|---|---|---|
| Sample | Main Peak Purity (%) | HMW (%) |
| AEX IP | 95.80 | 3.71 |
| AEX OP | 99.30 | 0.32 |

Table 20 shows 99% purity of main peak and 91% reduction of HMW which is determined by SE-HPLC.

Table 21 shows the results of Cation Exchange—High performance Liquid Chromatography comparing the main peak with acidic variants.

TABLE 21

| shows the results of Cation Exchange - High performance Liquid Chromatography comparing the main peak with acidic variants. CEX-HPLC Analysis | | |
|---|---|---|
| Sample | Main Peak (%) | Acidic Variants (%) |
| NPEL/AEX IP | 69.34 | 15.90 |
| AEX OP | 74.19 | 8.50 |

Table 21 shows 74% purity of main peak and approximately 46% reduction of acidic variants which is determined by CEX-HPLC.

Example 7—Purification of Monoclonal Antibody by Performing Affinity Chromatography Followed by AEX Chromatography Followed by CHT XT Resin (for 200 L Scale)

All chromatographic processes were carried out using an AKTA Pilot or AKTA Process system from GE Healthcare. Concentration of protein samples were determined by measuring absorbance at 280 nm using Spectrophotometer. CHT XT resin media obtained from Bio-rad. Chromatographic 300/250 columns were obtained from Millipore Corporation or GE Healthcare or Repligen. All Chemicals used during manufacturing process were of GMP grade.

A monoclonal antibody capable to bind to IgE expressed in Chinese Hamster Ovary (CHO) cell line is captured using Protein A (Mab Select Sure LX, GE Healthcare) packed in Chromatographic 250/250 column. Eluted protein is further subjected to viral inactivation and neutralization followed by depth filtration. After depth filtration, protein has been filtered by 0.2 μm filter.

Post depth filtration step, the protein mixture is further purified using Anion Exchange Chromatography resin (Poros HQ, Thermofisher) packed in Chromatographic 350/250 or 200/250 column.

Eluted protein from Anion Exchange Chromatography (AEX) is further polished using mixed-mode resin (CHT XT, Bio-rad) packed in Chromatographic 300/250 column. The residence time is 4 min/5 min for all the phases. After equilibration with Na Phosphate, pH 6.8 Anion exchange (AEX) output is loaded at maximum of 12.5 mg/mL of the resin. The column is washed using 3 CV, Na Phosphate, pH 6.8. Bound protein of interest is eluted using linear gradient between 40 mM Na Phosphate and 400 mM Na Phosphate, pH 6.8. Eluted peak of interest is analysed with SE-HPLC, CEX-HPLC for size and charge variants. The experimental design and process for CHT XT step is summarized in Table 22-24.

TABLE 22

| | | Experimental design for CHT XT | |
|---|---|---|---|
| Step | Buffer | Residence Time (min) | Column Volume (CV) |
| Sanitization | 0.5N Sodium Hydroxide | 4 to 5 | 3 CV and 0.5 hr hold |
| Charge | 400 mM Na Phosphate, pH 6.8 | 4 to 5 | 3 CV |
| Equilibration | 40 mM Na Phosphate, pH 6.8 | 4 to 5 | 3 CV or conductivity end point |
| Load | AEX Eluate + 40 mM Na Phosphate, pH 6.8 | 4 to 5 | Till loading volume |
| Wash | 40 mM Na Phosphate, pH 6.8 | 4 to 5 | 3 CV |
| Gradient Elution | Buffer A: Water Buffer B: 400 mM Phosphate, pH 6.8 from 10% to 24% B | 4 to 5 | 19 CV |
| Strip | 400 mM Phosphate, pH 6.8 | 4 to 5 | 3 CV |
| Sanitization | 0.5N Sodium Hydroxide | 4 to 5 | 3 CV and 0.5 hr hold |
| Storage | 0.1N Sodium Hydroxide | 4 to 5 | 3 CV |

TABLE 23

| | SE HPLC analysis of LMW SE-HPLC Analysis | |
|---|---|---|
| Sample | Main Peak Purity (%) | (%) LMW Variants |
| CHT IP | 99.30 | 0.43 |
| CHT OP | 99.90 | 0.01 |

TABLE 24

| | CEX HPLC-BV analysis CEX-HPLC Analysis | |
|---|---|---|
| Sample | Main Peak Purity (%) | (%) Basic Variants |
| CHT IP | 74.19 | 10.80 |
| CHT OP | 81.11 | 2.70 |

We claim:

1. A pharmaceutical composition comprising omalizumab and an acidic species or variant thereof, wherein the pharmaceutical composition comprises the acidic species or variant thereof in an amount of 11% or less as measured by cation exchange high performance liquid chromatography analysis; and wherein the pharmaceutical composition has omalizumab purity of at least 90%.

2. The pharmaceutical composition as claimed in claim 1, wherein the pharmaceutical composition has omalizumab purity of more than 90%.

3. The pharmaceutical composition as claimed in claim 1, wherein the pharmaceutical composition has omalizumab purity of more than 95%.

4. The pharmaceutical composition as claimed in claim 1, wherein the pharmaceutical composition has omalizumab purity of more than 96%.

5. The pharmaceutical composition as claimed in claim 1, wherein the pharmaceutical composition has omalizumab purity of more than 97%.

6. The pharmaceutical composition as claimed in claim 1, wherein the pharmaceutical composition has omalizumab purity of more than 98%.

7. The pharmaceutical composition as claimed in claim 1, wherein the pharmaceutical composition has omalizumab purity of more than 99%.

8. The pharmaceutical composition as claimed in claim 1, wherein the pharmaceutical composition comprises the acidic species or variant thereof in an amount of 10% or less as measured by cation exchange high performance liquid chromatography analysis.

9. The pharmaceutical composition as claimed in claim 1, wherein the pharmaceutical composition has omalizumab purity of at least 90% as measured by size exclusion high performance liquid chromatography.

10. The pharmaceutical composition as claimed in claim 1, wherein the pharmaceutical composition is prepared at 50 L scale.

11. The pharmaceutical composition as claimed in claim 1, wherein the pharmaceutical composition is prepared at 200 L scale.

12. The pharmaceutical composition as claimed in claim 1, wherein the pharmaceutical composition comprises the acidic species or variant thereof in an amount of 9% or less as measured by cation exchange high performance liquid chromatography analysis.

13. The pharmaceutical composition as claimed in claim 1, wherein the pharmaceutical composition comprises the acidic species or variant thereof in an amount of 8.5% or less as measured by cation exchange high performance liquid chromatography analysis.

14. The pharmaceutical composition as claimed in claim 1, wherein the pharmaceutical composition comprises the acidic species or variant thereof in an amount of 8% or less as measured by cation exchange high performance liquid chromatography analysis.

15. The pharmaceutical composition as claimed in claim 1, wherein the pharmaceutical composition maintains omalizumab quality at scale of 5 L, 50 L, and 200 L.

* * * * *